US012636251B1

(12) United States Patent
Doane

(10) Patent No.: US 12,636,251 B1
(45) Date of Patent: May 26, 2026

(54) GLYCOSIDE-CONTAINING AQUEOUS FORMULATIONS HAVING A LIPOPHILIC ACTIVE COMPONENT

(71) Applicant: Doane Technology Group LLC, Seattle, WA (US)

(72) Inventor: Braden Doane, Seattle, WA (US)

(73) Assignee: Doane Technology Group LLC, Seattle, WA (US)

( * ) Notice: Subject to any disclaimer, the term of this patent is extended or adjusted under 35 U.S.C. 154(b) by 0 days.

(21) Appl. No.: 18/653,593

(22) Filed: May 2, 2024

Related U.S. Application Data

(60) Provisional application No. 63/593,947, filed on Oct. 27, 2023.

(51) Int. Cl.
*A61K 9/107* (2006.01)
*A61K 31/00* (2006.01)
*A61K 45/06* (2006.01)

(52) U.S. Cl.
CPC ............ *A61K 9/107* (2013.01); *A61K 31/658* (2023.05); *A61K 45/06* (2013.01)

(58) Field of Classification Search
CPC ....... A61K 9/107; A61K 31/658; A61K 45/06
See application file for complete search history.

(56) References Cited

U.S. PATENT DOCUMENTS 8,551,507 B2 10/2013 Liu
2017/0348276 A1* 12/2017 Bryson ................ A61K 31/352
2019/0247449 A1* 8/2019 Avidov .................. A23K 50/10
2020/0054702 A1* 2/2020 Heller ................ A61K 36/3482
2021/0068400 A1* 3/2021 Avidov ................... C05B 17/00
2022/0218773 A1* 7/2022 Schaneville ....... A61K 36/3482
2024/0207340 A1* 6/2024 Schaneville ........... A61K 47/36

OTHER PUBLICATIONS

Mao, G. et al. "Enzymatic Synthesis and Structural Characterization of Rebaudioside D3, a Minor Steviol Glycoside of Stevia rebaudiana Bertoni" American Journal of Plant Sciences, 2017, 8, 441-450 (Year: 2017).*
Banerjee et al., "Synthesis, characterization and stress-testing of a robust quillaja saponin stabilized oil-in-water phytocannabinoid nanoemulsion," Journal of Cannabis Research, (2021).
Luo et al., "Evaluation of Mogroside V as a Promising Carrier in Drug Delivery: Improving the Bioavailability and LiverDistribution of Silybin," AAPS PharmSciTech, (2020).
Wolfrum et al., "A renaissance of soaps?—How to make clear and stable solutions at neutral pH and room temperature," Advances in Colloid and Interface Science, (2016).
Zhang et al., "Steviol glycosides, an edible sweet surfactant that can modulate the interfacial and emulsifying properties of soy protein isolate solution," Journal of Food Engineering (2021).
Zhang et al., "Solubilisation and Enhances Oral Absorption of Curcumin Using a Natural Non-Nurtitive Sweetener Mogroside V," International Journal of Nanomedicine, (2022).

* cited by examiner

*Primary Examiner* — Andrew S Rosenthal
(74) *Attorney, Agent, or Firm* — CHRISTENSEN O'CONNOR JOHNSON KINDNESS PLLC

(57) ABSTRACT

Glycoside-containing aqueous formulations having a high lipophilic active component (LAC) to surfactant ratio are described. The aqueous formulations can be used to efficiently deliver LAC through a variety of formulation types, including beverages.

21 Claims, No Drawings

GLYCOSIDE-CONTAINING AQUEOUS FORMULATIONS HAVING A LIPOPHILIC ACTIVE COMPONENT

CROSS-REFERENCE TO RELATED APPLICATION

This application claims the benefit of U.S. Provisional Patent Application No. 63/593,947, filed on Oct. 27, 2023, which is hereby incorporated by reference in its entirety.

BACKGROUND

A number of lipophilic components that have beneficial physiological effects are difficult to formulate into liquid carriers for administration. Cannabinoids are one such lipophilic component, having a water-solubility of less than 1 µg/ml.

Attempts to prepare oral formulations of cannabinoids have involved preparing capsules or formulations in alcohol or using various emulsification approaches that require large amounts of carriers and surfactants. For example, achieving desired package and serving sizes of cannabinoids in beverages (upwards of 100 mg per ounce) requires elevated concentrations of surfactants, often well beyond the quantities generally recognized as safe (GRAS) for use in beverages and possibly in the range where toxicological issues arise.

The major classes of surfactants currently used include saponins, fatty acid sucrose esters (e.g., sucrose palmitate), lecithins (e.g., phosphatidylcholines, glycerophospholipids), and fatty esters or polyoxylated esters of sorbitan (e.g., polysorbate 80, sorbitan monooleate).

Saponin is a natural extract of the soap bark tree. When highly purified (type 2, >98%), saponins are a great natural emulsifier for cannabinoids, however, they have a somewhat bitter aftertaste and create foaming issues during manufacture. Used alone, saponins also typically demand concentrations well beyond the generally recognized as safe (GRAS) limits for beverages to successfully emulsify standard quantities of cannabinoids.

Sucrose esters, while including two natural components that have been chemically conjugated, are artificial molecules and have either consumer perception or regulatory limits on use. Lecithins have poor mouth feel and taste. Synthetic surfactants do not allow the growing consumer demands for "clean labels" (i.e., natural or naturally-occurring ingredients only) to be met.

Thus, strong currently available surfactants lead to one or more of foaming during manufacture, poor mouth feel (soapy) and taste (bitter and long-lasting), consumer perception or regulatory limits on use, and failure to meet growing consumer demands for "clean labels" (i.e., natural or naturally-occurring ingredients only) to be met.

Some high-intensity sweeteners are terpenoid glycosides. For example, mogrosides are a family of triterpenoid glycosides found naturally-occurring in Siraitia grosvenorii (Swingle, Lo Han Guo) whereas steviosides and rebaudiosides are related families of diterpenoid glycosides found naturally-occurring in *Stevia rebaudiana* (*Stevia*). These high-intensity terpenoid glycosides have found burgeoning use in beverages as non-caloric sugar replacements at low concentrations. Although roughly in the range of 200-500 times the sweetness of sucrose, above about 100 ppm (0.01 wt. %) these high-intensity sweeteners exhibit a number of negative organoleptic properties, including a metallic off-taste, temporally delayed/extended flavor impacts and what has been termed the disturbing "pain effect" believed to be the result of the glycosides coating the tongue and oral cavity.

*Quillaja* saponins are a class of diterpenoid glycosides extracted from *Quillaja saponaria* (Soapbark Tree) and appear to be the only terpenoid glycosides that have found utility in beverages for surfactant and foam-enhancing properties. Unlike mogrosides, steviosides, and rebaudiosides, which are also terpenoid glycosides, *Quillaja* saponins do not have sweet organoleptic properties. They are not high-intensity sweeteners. However, *Quillaja* saponins do share a variety of the negative organoleptic properties of the high-intensity sweeteners even at moderate concentrations.

Recent publications have reported the use of various terpenoid glycosides, including mogrosides and steviosides, as so-called biosurfactants that have found utility in fabricating solid dispersions between one glycoside and one lipophilic compound. These solid dispersions are described as creating core-shell micelles where the lipophilic compound occupies the core and the terpenoid glycoside creates the shell. All reported references utilize an excess—and often a 10× or 20× excess—of glycosides to lipophilic compound to achieve solubility enhancement of the lipophilic compounds. This abundant excess of glycosides in their use as biosurfactant has been explained as necessary given the ability of the glycoside shell to completely surround the lipophilic compound in three dimensions to enable effective micellization.

The extreme limits of this functional utility by detailing how the glycoside solubilizers were found to be particularly effective from about 5 to about 40% w/v solubilizer of the entire solution and preferably about 10% w/v solubilizer is discussed in recent reports. This equates to a concentration around 10,000 ppm and one that exceeds the threshold of negative organoleptic aspects for these glycoside high-intensity sweeteners, including the pain effect, by several orders of magnitude. Additionally, this same patent also utilizes a consistent loading of 2 mg of lipophilic substance in 1 ml of 10% glycoside solution. That equates to a paltry concentration of lipophilic active of only 0.2% and, perhaps more limitingly, a glycoside to lipophilic ratio of 50:1. Clearly, such high ratios of glycoside to lipophilic compound prohibits the application of such technology in beverage applications since the negative organoleptic threshold of high intensity sweeteners (>100 ppm) limits lipophilic active concentrations to parts-per-billion (ppb) levels.

The synergistic effects of steviol glycosides on soy protein isolate (SPI) as a primary surfactant has been recently reported. This study was limited to SPI as the only reported anionic and proteinaceous surfactant. In fact, the researchers demonstrated that the synergistic effect of steviol glycosides appeared to involve the decrease (made more negative) of zeta potential by −10 mV as compared to SPI alone. Furthermore, modeling studies by the authors demonstrated that the synergistic effect was mechanistically reliant upon the docking of steviol glycosides at a specific binding pocket on the SPI protein structure. As a result, this synergistic effect of steviol glycosides would be expected to be limited to either occurring with anionic surfactants, protein surfactants or both, including the possibility that it is limited to soy protein alone and no other proteins.

Other reports demonstrate the ability of rebaudioside A (Reb A) to act synergistically with fatty acid salts, namely sodium oleate, to produce more stable blank emulsions using corn oil as lipid carrier oil, than can be achieved with sodium oleate alone. Unfortunately, these reports do not disclose loading any lipophilic substances into this case-study emulsion, so it is unclear what percentage loadings to expect of this system. However, considering that oleate is also an anionic surfactant and the authors theorized that the hydroxyl groups of Reb A would need to interact with the anionic carboxylate moiety of the oleate, it seems clear that this system would be expected to be restricted to anionic surfactants and glycosides mechanistically impact the system by stimulating a more negative zeta potential.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In an aspect, an aqueous formulation is presented that comprises at least one glycoside; a surfactant; a lipophilic active component (LAC); where the LAC comprises at least one cannabinoid; where the aqueous formulation has a concentration of the first LAC ranging from about 0.0001 to about 50.0 w/v %; where the aqueous formulation contains an effective amount of at least 0.1 μg/kg body weight of LAC; and where the aqueous formulation is a stable emulsion.

DETAILED DESCRIPTION

While illustrative embodiments have been illustrated and described, it will be appreciated that various changes can be made therein without departing from the spirit and scope of the invention.

In an aspect, an aqueous formulation is presented that comprises at least one glycoside; a surfactant; a lipophilic active component (LAC); where the LAC comprises at least one cannabinoid; where the aqueous formulation has a concentration of the first LAC ranging from about 0.0001 to about 50.0% w/v; where the aqueous formulation contains an effective amount of at least 0.1 μg/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one vitamin; where the aqueous formulation has a concentration of the first LAC ranging from about 0.0001 to about 50.0 w/v %; where the aqueous formulation contains an effective amount of at least 0.01 μg/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one fatty acid, mono-, di-, or triglyceride where the fatty acid, mono-, di-, or triglyceride has at least one carbon-carbon double bond; where the aqueous formulation has a concentration of the first LAC ranging from about 0.0001 to about 50.0 w/v %; where the aqueous formulation contains an effective amount of at least 0.1 μg/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one of linolenic acid and its salts or esters, eicosapentaenoic acid and its salts or esters, or docosahexaenoic acid and its salts or esters; where the aqueous formulation has a concentration of the first LAC ranging from about 0.0001 to about 50.0 w/v %; where the aqueous formulation contains an effective amount of at least 0.1 μg/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one fatty alcohol where the fatty alcohol has at least one carbon-carbon double bond; where the aqueous formulation has a concentration of the first LAC ranging from about 0.0001 to about 50.0 w/v %; where the aqueous formulation contains an effective amount of at least 0.1 μg/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one silicone or fluorocarbon; where the aqueous formulation has a concentration of the first LAC ranging from about 0.0001 to about 50.0 w/v %; where the aqueous formulation contains an effective amount of at least 0.1 μg/kg body weight of LAC; and where the aqueous formulation is a stable emulsion.

In another aspect, an aqueous formulation is presented that comprises at least one glycoside; a surfactant; a lipophilic active component (LAC); where the LAC make it possible to create a palatable beverage or product; where the aqueous formulation has a concentration of the first LAC ranging from about 0.0001 to about 50.0 w/v %; where the aqueous formulation contains an effective amount of at least 0.1 μg/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one phospholipid; where the aqueous formulation has a concentration of the first LAC ranging from about 0.0001 to about 50.0 w/v %; where the aqueous formulation contains an effective amount of at least 0.1 ug/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one compound of cannabimimetic lipid amide; where the aqueous formulation has a concentration of the first LAC ranging from about 0.0001 to about 50.0 w/v %; where the aqueous formulation contains an effective amount of at least 0.1 ug/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one flavonoid; where the aqueous formulation has a concentration of the first LAC ranging from about 0.0001 to about 50.0 w/v %; where the aqueous formulation contains an effective amount of at least 0.1 ug/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one terpenoid; where the aqueous formulation has a concentration of the first LAC ranging from about 0.0001 to about 50.0 w/v %; where the aqueous formulation contains an effective amount of at least 0.1 ug/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one phenol; where the aqueous formulation has a concentration of the first LAC ranging from about 0.0001 to about 50.0 w/v %; where the aqueous formulation contains an effective amount of at least 0.1 ug/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one terpenoid; where the aqueous formulation has a concentration of the first LAC ranging from about 0.0001 to about 50.0 w/v %; where the aqueous formulation contains an effective amount of at least 0.1 ug/kg body weight of LAC; and where the aqueous formulation is a stable emulsion.

In another aspect, an aqueous formulation is presented that comprises at least one glycoside; a surfactant; a lipophilic active component (LAC); where the LAC comprises at least one polyketide; where the aqueous formulation has a concentration of the first LAC ranging from about 0.0001 to about 50.0 w/v %; where the aqueous formulation contains an effective amount of at least 0.1 ug/kg body weight of LAC; and where the aqueous formulation is a stable emulsion.

For the purposes of this disclosure, "a stable emulsion" is defined as the disclosed aqueous LAC formulations remaining in a consumable and/or useable condition for at least 6 months and contains particles that resist Ostwald ripening.

In an embodiment the aqueous formulation where the formulation is stable at a temperature of −86° C. to 50° C. In a further embodiment the aqueous formulation where the formulation is stable at a temperature of 0° C. to 40° C. In a further embodiment the aqueous formulation where the formulation is stable at a temperature of 2° C. to 25° C.

In an embodiment the aqueous formulation is stable for at least 12 months.

In an embodiment the aqueous formulation is used for a particular purpose where the purpose of the formulation is a beverage product, an ingestible product, an inhalable product, an ocular product, a topical product, or a pharmaceutical product.

In an embodiment the aqueous formulation is a beverage where the beverage product is beer, coffee, tea, soda, juice or juice flavored drink, carbonated, or any combination thereof.

In an embodiment the aqueous formulation is a topical product where the topical product is a cream, a lotion, an ointment, a gel, a paste, a spray, or any combination thereof.

In an embodiment the aqueous formulation is a tropical product where the topical product is a transdermal patch.

The current disclosure provides lipophilic active component (LAC) emulsion formulations with improved taste and performance. The use of specific flavor and sweetener agents unexpectedly facilitates emulsification and stabilizes the resulting emulsions, thus decreasing the quantity of standalone surfactants necessary. High ratios of LAC to glycosides and high LAC loadings make it possible to create a palatable beverage. Without these features the threshold concentration of high-intensity sweetener would create an undrinkable and, in some cases, painful beverage to consume.

The present disclosure provides singular or multiple glycoside with singular or multiple surfactant in combinations to yield aqueous formulations having a LAC. The aqueous formulations include at least one glycoside, a surfactant, and a LAC. According to aspects of the current disclosure, commercially available glycosides (excluding saponins), by themselves or in combination, are not capable of emulsifying a LAC. However, with addition of less than 10% molar equivalent (ca. 1:10 surfactant to glycoside or glycosides) the combination can emulsify a LAC. This is not simply the result of the surfactant because the total quantity of surfactant required is 1/10th that of what would be required for emulsifying the same quantity of LAC if only the surfactant were used.

The aqueous formulations can include five to ten times more LAC than individual glycosides or two times more LAC than total glycosides. For example, the ratio of LAC to an individual glycoside can be 5:1, 6:1, 7:1, 8:1, 9:1, 10:1 or higher. The ratio of LAC to total glycosides can be 1:1, 1.5:1, 2:1 or higher.

In some embodiments the aqueous formulation can have the ratio of the LAC to an individual glycoside is 5:1, 6:1, 7:1, 8:1, 9:1, 10:1 or higher from about 2:1 to about 20:1.

In some embodiments the aqueous formulation can have the ratio of the LAC to the total glycosides can be 1:1, 1.5:1, 2:1 or higher from about 2:1 to about 20:1, from about 3:1 to 10:1 and from about 4:1 to 7:1.

Aqueous formulations disclosed herein also allow LAC content in excess of 5% by weight. For example, aqueous formulations disclosed herein can include LAC at 5% by weight, 6% by weight, 8% by weight, 10% by weight, 15% by weight, 20% by weight, 25% by weight and 50% by weight. This benefit was also unexpected given the teachings in the current literature which describes lipophilic component loading of 0.2% by weight while using fifty times excess of glycoside.

Aqueous formulations disclosed herein can maintain stability achieved at high LAC content even when diluted 100 to 1000-fold in an aqueous formulation, for example to form a beverage. This feature would not have been predicted according to several reports describing the model of critical micelle concentrations and Krafft temperatures.

The aqueous formulations also do not require a lipophilic carrier oil or a particular surfactant type for functionality. These features were unexpected because of reports that it is necessary to use a carrier oil to create a cannabinoid emulsion. It has been demonstrated that increasing the zeta potential magnitude on soy protein isolate and glycoside "docking" at a key position on soy protein isolate was required to produce the impact reported while Wolfrum (2016) demonstrated a case study emulsion using a single anionic surfactant, sodium oleate, and did not load lipophilic substances into the emulsion.

In some embodiments the aqueous formulations can have the surfactant selected from an ionic surfactant, an anionic surfactant, a cationic surfactant, a zwitterionic surfactant, a non-ionic surfactant or any combination thereof.

In some embodiments the aqueous formulations can have the surfactant hydrophilic-lipophilic balance from about 7 to about 19.

In some embodiments the aqueous formulations can have the surfactant be a sorbitan fatty acid ester, polyethylene glycol sorbitan fatty acid ester, saturated polyglycolized glyceride, *quillaia*, polyethylene glycol stearate, polyethylene glycol hydrogenated castor oil, propylene glycol laurate, D-alpha-tocopherol polyethylene glycol 1000 succinate (TPGS), lecithin, sucrose laurate, sucrose palmitate, sucrose stearate, gamma-cyclodextrin, beta-cyclodextrin, whey protein, caseinate, polyethylene glycol hydroxystearate polyoxyl-10-oleyl ether, polyethylene glycol glyceride, Tween 20, Tween 40, Tween 60, Tween 65, Tween 80, Tween 85, Span 20, Span 40, Span 60, Span 65, Span 80, Span 85, coco glucoside, decyl glucoside, caprylyl glucoside, cocamidopropyl betaine, coco betaine, disodium laureth sulfosuccinate, lauryl glucoside, coco glucoside, decyl glucoside, lauryl glucoside, disodium laureth sulfosuccinate, sodium coco sulfate, plantapon SF, soap nuts, yucca extract, shikakai powder, soapwort, cholesterol, phytosterol, monoglyceride, lanolin, or combinations thereof.

The singular glycoside or combination of glycosides may include a steviol-type glycoside and a curcurbitane-type glycoside. The glycoside or combination of glycosides may include a terpene glycoside. The singular glycoside or combination of glycosides may include a diterpenoid glycoside and/or a triterpenoid glycoside. The singular glycoside or combination of glycosides may include rebaudioside and/or mogroside. Most rebaudiosides and mogrosides are generally regarded as high-intensity sweeteners (HIS), while the presence of sweetening functionality and intensity appears to be related to the number of glycoside units present in mogroside and rebaudioside species.

The singular glycoside or combinations of glycosides can be selected from the classes of steviol, curcurbitane, diterpenoid, triterpenoid, steroid glycoside, rebaudioside, mogroside, thioglycoside, iridoid glycoside, cardiac glycoside, phenolic glycoside, flavonoid glycoside, hesperidin, naringin, rutin, quercitrin, cyanogenic glycosides, benzo-gamma-pyrone, alcoholic glycosides, anthraquinone glycosides, coumarin glycosides, chromone glycosides, or any combination thereof.

In an embodiment the combination of glycosides can include a mixture of one or more rebaudiosides and one or more mogrosides.

There are two major classes of terpene glycosides: monodesmosidic where there is only a single sugar chain attached at C-3 and bidesmosidic where a second sugar chain is also attached at C-24 or C-28. It is theorized that the *quillaja* extract including predominantly monodesmosidic saponins alters the three-dimensional conformations of bidesmosidic glycosides to orient and align the polar and apolar moieties. Without being limited by theory, this alignment functions to create surfactant properties.

Present in the emulsion may be natural stabilizers in each phase: vitamin c in the aqueous phase, ascorbyl palmitate and/or tocopheryl succinate in the surfactant phase, and vitamin e in the oil phase.

Within certain examples described herein, aqueous refers to any liquid composition in which the majority of the liquid component is water. In certain examples, aqueous refers to any liquid composition in which the liquid component is pure water. Other examples include liquid compositions in which the liquid component is at least 80% water, at least 85% water, at least 90% water, at least 95% water, or at least 98% water, or at least 99% water.

The current disclosure provides aqueous formulations having high LAC concentrations and high LAC to surfactant ratios. The aqueous formulations can be used to efficiently deliver active components and/or active ingredients, such as cannabinoids.

A glycoside is any molecule in which a sugar group (the glycone) is bonded through its anomeric carbon to another group (the aglycone), which may or may not be another carbohydrate, via a glycosidic bond. Glycosides can be linked by an O- (an O-glycoside), N- (a glycosylamine), S- (a thioglycoside), or C- (a C-glycoside) glycosidic bond.

The term 'glycoside' is a general one which embraces all the many and varied combinations of sugars and aglycones. More precise terms are available to describe particular classes. Terms used for aglycones are generally self-explanatory (e.g., phenol, anthraquinone and sterol glycosides). The names 'saponin' (soap-like), 'cyanogenetic' (producing hydrocyanic acid) and 'cardiac' (having an action on the heart), although applied to these substances when little was known about them, are useful terms which do in fact bring together glycosides of similar chemical structure.

The flavor and sweetener agents that unexpectedly facilitate emulsification are included within the class of terpene glycosides. Rebaudiosides (REB), found naturally-occurring in *Stevia rebaudiana*, are steviol-type diterpene glycosides, and mogrosides (MOG), found naturally occurring in Siraitia grosvenorii, are curcurbitane-type triterpene glycosides. The structure of steviol and curcurbitane are shown below

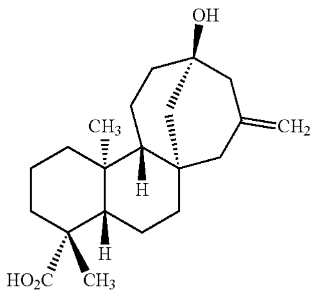

Steviol

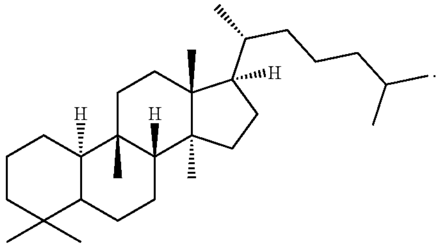

Curcurbitane

Natural terpene glycosides are well known and exist in a variety of plant sources. They generally are terpene aglycons attached to at least one glucose or other simple sugars (e.g., xylose or galactose), and the most common forms are monoterpene glycosides, diterpene glucosides, and triterpene glucosides. Many of these compounds are known to be non-toxic and natural sweeteners.

Monoterpene glycosides consist of a monoterpene (2 isoprene units) aglycone bound to a glycone group of one, two, three, or more sugar residues. Exemplary monoterpene glycosides include paeoniflorin, albiflorin, geniposide, rosiridin, monoterpenol dihexose pentose 1, monoterpenol hexose pentose 1, monoterpenol hexose pentose 2, monoterpenol glucoside 1, monoterpenol hexose pentose 3, monoterpenol glucoside 2, monoterpenol glucoside 3, monoterpenol hexose deoxyhexose 1, monoterpenol hexose pentose 4, malonylated monoterpenol glucoside 1, monoterpenol hexose pentose 5, malonylated monoterpenol glucoside 2, monoterpenol hexose pentose 6, monoterpenol hexose pentose 7, malonylated monoterpenol glucoside 3, monoterpenol hexose pentose 8, monoterpenol hexose deoxyhexose 2, malonylated monoterpenol glucoside 4, decyl-beta-D-glucopyranoside, paeonihybridin, paeobrin, salicylpaeoniflorin, 6-O-beta-D-glucopyranosyl-8-O-benzoyl-paeonisuffrone, 9-epi-paeonidanin, paeonidanin, 3-methyl-O-[alpha-arabinopyranosyl-(1-6)-beta-glucopyranosyl]-6-methyl-benzofuran, (3S)-hydroxylterpane-10-O-beta-D-glucopyranoside, (3R)-hydroxylterpane-10-O-beta-D-glucopyranoside. Exemplary monoterpene glycosides include glycosides of limonene, geraniol, geranyl acetate, linalool, alpha-terpineol, alpha-pinene, sabinene, beta-myrcene, delta-3-carene, beta-pinene, alpha-thujene, gamma-terpinene, alpha-terpinolene, terpinen-4-ol, alpha-terpinene, nerol, isomenthone, perillyl alcohol, perillic acid, and dihydroperillic acid.

Diterpene glycosides consist of a diterpene (4 isoprene units) aglycone bound to a glycone group of one, two, three, or more sugar residues. Exemplary diterpene glycosides include, steviol glycosides such as rebaudioside, rebaudioside D, rebaudioside A, rebaudioside N, rebaudioside M, rebaudioside E, stevioside, steviol monoside, steviolbioside, rubusoside, rubusoside A, dulcoside B, dulcoside A, rebaudioside B, rebaudioside G, rebaudioside C, rebaudioside F, rebaudioside I, rebaudioside H, rebaudioside L, rebaudioside K, rebaudioside J, rebaudioside M2, rebaudioside D2, rebaudioside S, rebaudioside T, rebaudioside U, rebaudioside V, rebaudiosides W, rebaudioside Z1, rebaudioside Z2, rebaudioside IX, and enzymatically glucosylated steviol glycosides. The structure of rebaudioside A is shown below. Other diterpenes that contain various numbers of glucose moieties are known in the art. These compounds include: paniculoside IV, suaviosides A, B, C1, D1, D2, E, F, G, H, I, and J.

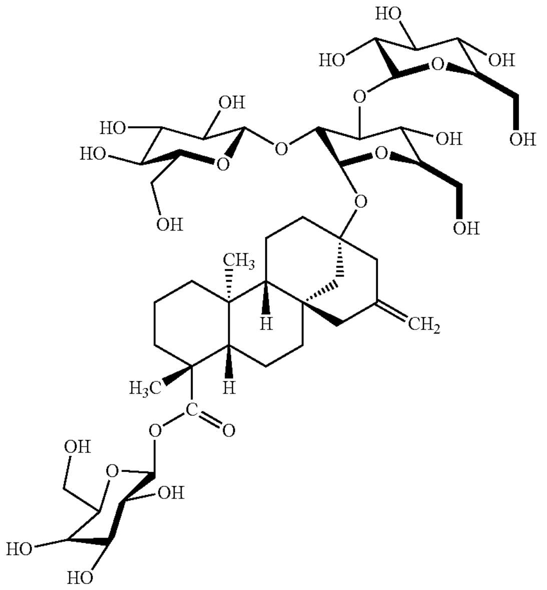

Rebaudiode A

Triterpene glycosides consist of a triterpene (6 isoprene units) aglycone bound to a glycone group of one, two, three, or more sugar residues. Exemplary triterpene glycosides include mogrosides, astragaloside, astragaloside IV, actein, cimicifugoside, cimigoside, 20-hydroxy-11-oxomogroside IA1, 11-oxomogroside V, 11-oxomogroside IA1, mogroside ME, mogroside III, mogroside IV, mogroside V, siamenoside I, triterpenoid glycoside V, neogroside, kaempferol-7-alpha-L-rhamnopyranoside, kaempferol-3,7-alpha-L-dirhamnopyranoside, 11-oxomogroside III, 11-dehydroxymogroside III, 11-oxomogroside IV, mogroside II, mogroside VI, 11-oxo-mogroside and siamcroside-1, 23-epi-26 deoxyactein, cimiracemoside A, 27-deoxyactein, 26-deoxycimicifugoside, acetyl shengmanol xyloside, cimicifugoside (cimigenol-3-O-beta-D-xylopyranoside), cimiaceroside A, 12-beta-hydroxycimigenol-3-O-beta-D-xylopyranoside, 12beta-hydroxycimigenol-3-O-alpha-L-arabinopyranoside, 21-hydroxycimigenol-3-O-alpha-L-arabinopyranoside, 21-hydroxycimigenol-3-O-beta-D-xylopyranoside, cimigenol-3-O-alpha-L-arabinopyranoside, 12beta-acetoxycimigenol-3-O-alpha-L-arabinopyranoside, 24-acetylisodahurinol-3-O-beta-D-xylopyranoside, 20(S),22(R),23(S),24(R)-16beta:23;22;:25-diepoxy-12beta-acetoxy-3beta,23,24-trihydroxy-9,19-cycloanost-7-ene-3-O-beta-D-xylopyranoside, 20(S),22(R),23(S),24(R)-16beta:23;22;:25-diepoxy-12beta-acetoxy-3beta,23,24-trihydroxy-9,19-cycloanost-7-en-3-O-beta-L-arabinopyranoside, and 20(S),22(R),23(S),24(R)-16beta:23;22;:25-diepoxy-12beta-acetoxy-3beta,23,24-trihydroxy-9,19-cycloanostane-3-O-beta-D-xylopyranoside. Exemplary triterpene glycosides also include glycosides of amyrin, such as alpha-amyrin beta-amyrin and delta-amyrin as shown below

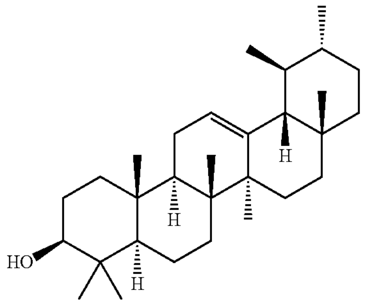

α-Amyrin

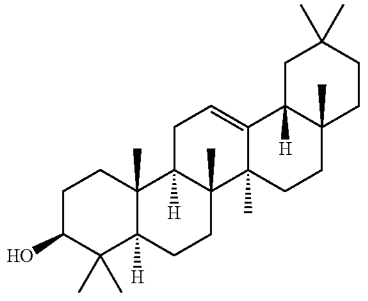

β-Amyrin

-continued

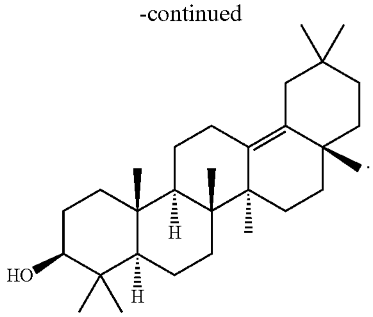

δ-Amyrin

Exemplary mogrosides include grosmogroside I, mogroside IA, mogroside IE, 11-oxomogroside IA, mogroside II, mogroside II A, mogroside IIB, mogroside II E, 7-oxomogroside II E, mogroside III, mogroside IIIe, 11-deoxymogroside III, mogroside IV, 11-oxomogroside IV, 11-oxomogroside IV A, mogroside V (shown below), isomogroside V, 11-deoxymogroside V, 7-oxomogroside V, 11-oxomogroside V, isomogroside V, mogroside VI, mogrol, 11-oxomogrol, siamenoside I and combinations thereof.

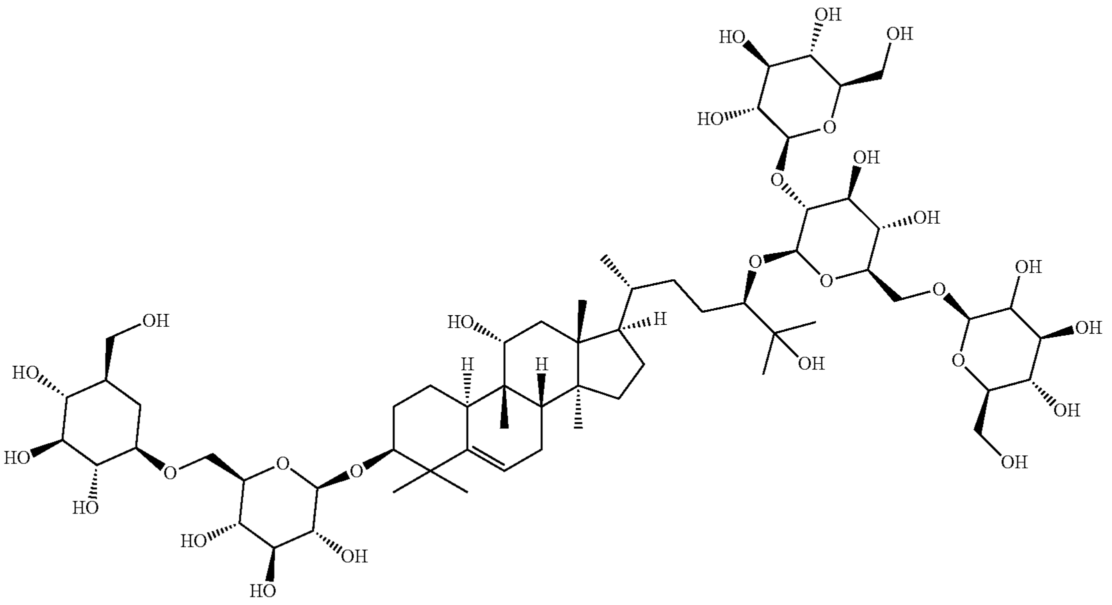

Morgroside V

There are two major classes of terpene glycosides: monodesmosidic where there is only a single sugar chain attached at C-3 and bidesmosidic where a second sugar chain is also attached at C-24 or C-28.

Saponins are naturally occurring amphiphilic glycosides, which contain polar glycone structure moieties (sugars) separated from nonpolar aglycones structure moieties (also known as sapogenins). Saponin glycosides mostly originated from plants, such as the *Quillaja* plant (shown below), licorice root, and *Camellia* plants, and tend to foam with water.

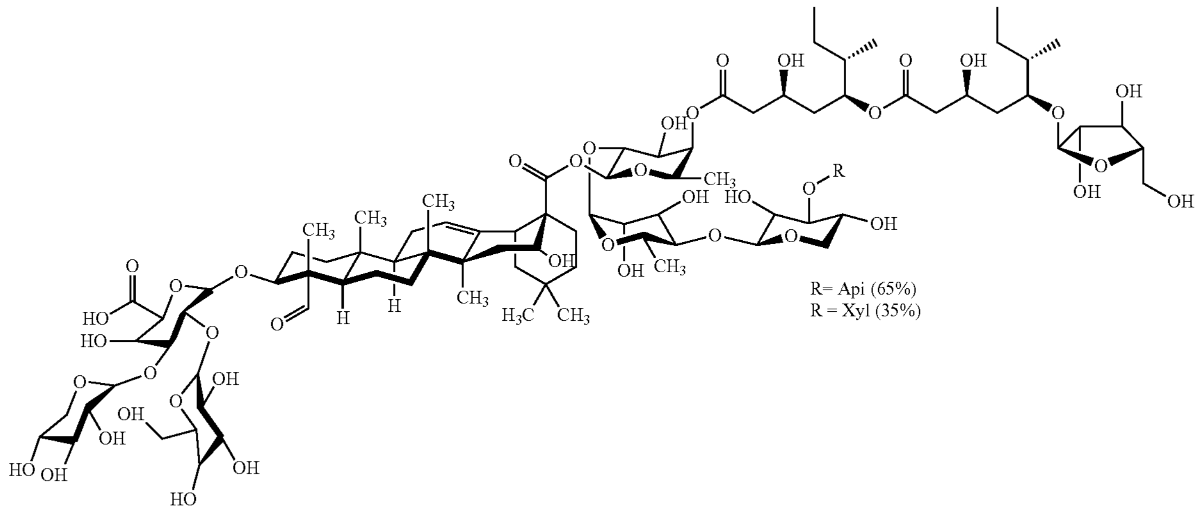

Saponin Glycoside from the Quillaja Plant

Saponins are classified according to their aglycone counterparts as (i) steroidal saponins and (ii) triterpenoid saponins. The difference between these two classes is that the steroidal saponins are molecules with 27 C-atoms whereas the triterpenoid saponins are molecules with 30 C-atoms. Triterpenoid saponins are further subcategorized into (i) oleanane saponins (e.g., *Sapindus mukorossi, Camellia oleifera*, etc.) (ii) ursolic acid saponins (e.g., *Ilex paragariensis*) and (iii) dammarane saponins (e.g., *Panax gingseng*). Steroid saponins are also further divided into furostanol type and spirostanol type. Saponins from some families such as Solanaceae have steroidal glycoalkaloids as aglycone backbone. Based on number of sugar units, saponins are classified into (i) monodesmosidic saponins, which have a single sugar unit attached to carbon-3, (ii) bidesmosidic saponins having two sugar units attached to C-3 and C-26 or 28 and (iii) tridesmosidic saponins: a compound that consists of three sugar units attached. Branched or linear chains of sugars are attached to the aglycone. These sugar units are mostly composed of D-glucose (Glc), D-galactose (Gal), L-arabinose (Ara), L-rhamnose (Rha), D-xylose (Xyl), D-fructose (Fuc), and glucuronic acid (GlcA) [21,22]. The ginsenosides are triterpene glycosides and ginseng saponins from *Panax ginseng* (Chinese ginseng) and *Panax quinquefolius* (American ginseng). Exemplary saponin glycosides include saponin from *Quillaja*, furostan saponins, glycyrrhizin, escin (aescin), and tea saponin.

Furostan saponins of natural occurrence are bidesmosides in which a glucose monosaccharide is attached at the 26-OH group of the aglycone (with few exceptions), and an oligosaccharide chain is usually connected at 3-OH. The structure of furostan is shown below

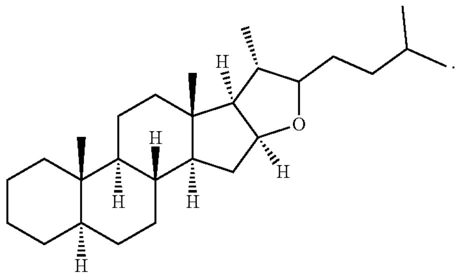

Glycyrrhizin is a triterpenoid saponin glycoside derived from licorice root, which occurs as a mixture of calcium and potassium salts of glycyrrhizic acid. The structure of glycyrrhizic acid is shown below

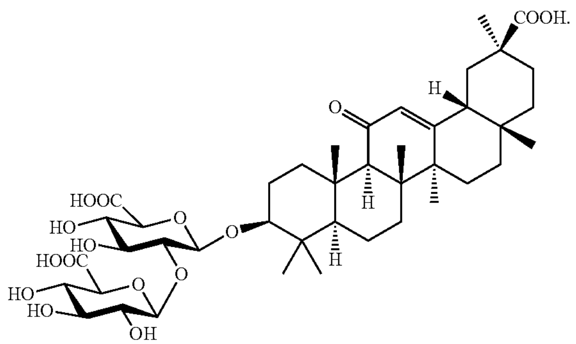

Escin or aescin is a mixture of saponins with anti-inflammatory, vasoconstrictor and vasoprotective effects found in *Aesculus hippocastanum* (the horse chestnut). Escin is the main active component in horse chestnuts and is responsible for most of its medicinal properties. The main active compound of escin is beta-aescin, although the mixture also contains various other components including alpha-aescin, protoescigenin, barringtogenol, cryptoescin and benzopyrones. The structure of escin is shown below

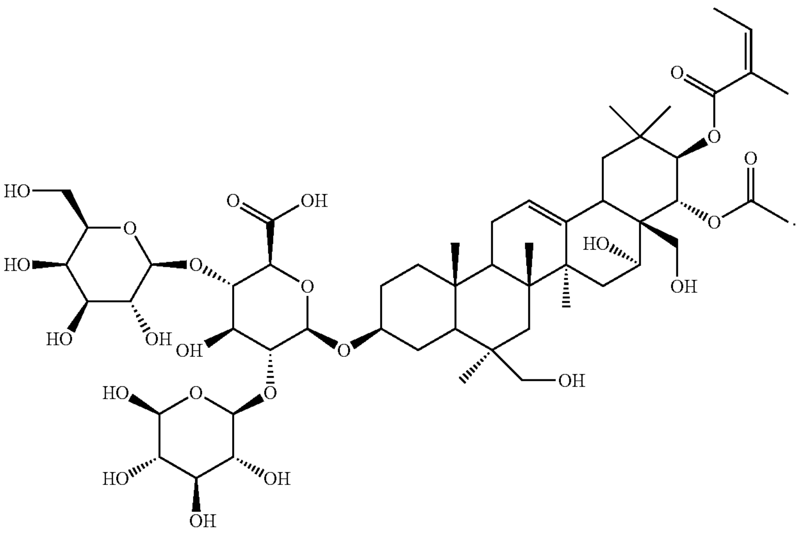

Escin

The structure of a tea saponin, found in *Camellia* plants, is shown below

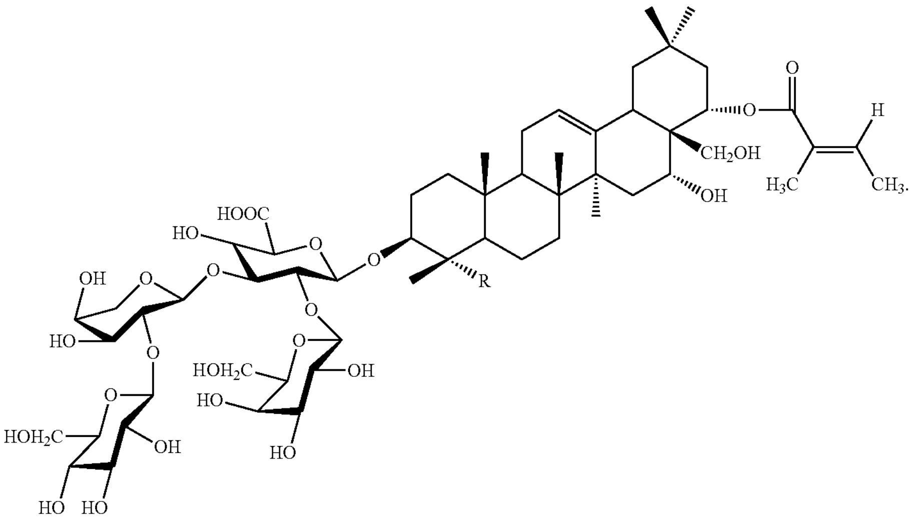

Surfactants can be classified as nonionic, anionic, cationic, or amphoteric depending on the charge of the hydrophilic head. Nonionic surfactants are neutral and do not have any charge on their hydrophilic end. Anionic surfactants have a negative charge while cationic surfactants have a positive charge on their hydrophilic end. Amphoteric surfactants, also referred to as zwitterionic surfactants, can have either a positive, negative, or neutral net charge on their hydrophilic end depending on the pH of the environment. In acidic environments, the amphoteric surfactant behaves like a cationic surfactant and in alkaline environments, it behaves like an anionic surfactant.

Nonionic surfactants include sorbitan esters, polyethylene glycol sorbitan fatty acid esters, polyoxyethylene alkyl ethers, polyoxyethylene fatty acid esters, polyethylene-polypropylene glycols, saturated polyglycolized glycerides, polyethylene glycols, *quillaia*, polyethylene glycol stearates, polyethylene glycol glycerides, sucrose esters of fatty acids, and chemical equivalents.

Sorbitan esters include sorbitan monolaurate, sorbitan monopalmitate, sorbitan monostearate, sorbitan tristearate, sorbitan monooleate, and sorbitan trioleate.

Polyethylene glycol sorbitan fatty acid esters include polyethylene glycol sorbitan monolaurate (polysorbate 20), polyethylene glycol sorbitan monopalmitate (polysorbate 40), polyethylene glycol sorbitan monostearate (polysorbate 60), polyethylene glycol sorbitan tristearate (polysorbate 65), polyethylene glycol sorbitan monooleate (polysorbate 80), polyethylene glycol sorbitan trioleate (polysorbate 85), polyethylene glycol sorbitan hexaoleate, and polyethylene glycol sorbitan tetraoleate.

Polyoxyethylene fatty acid esters include polyoxyl 40 hydrogenated castor oil.

Polyethylene-polypropylene glycols include polyethylene-polypropylene glycol (poloxamer) 124, poloxamer 188, poloxamer 407, poloxamer 108, poloxamer 217, poloxamer 238, poloxamer 288, poloxamer 338, poloxamer 182, poloxamer 183, poloxamer 212, poloxamer 331, or poloxamer 335.

Saturated polyglycolized glycerides include lauroyl macrogol-32 glycerides.

Polyethylene glycols include polyethylene glycol (PEG) 400.

*Quillaia* include *quillaia/quillaja* saponins or *quillaia* extract.

Polyethylene glycol stearates include PEG 8 stearates or PEG 40 stearates.

Polyethylene glycol hydrogenated castor oils include PEG 25 hydrogenated castor oil and PEG 40 hydrogenated castor oil.

Polyethylene glycol glycerides include PEG 8 caprylic/capric glycerides or PEG 300 oleic glycerides.

Sucrose esters of fatty acids include sucrose distearate, sucrose dilaurate, sucrose palmitate.

Common anionic surfactants include dioctyl sodium sulfosuccinate (DOSS), perfluorooctanesulfonate (PFOS), linear alkylbenzene sulfonates, sodium lauryl ether sulfate, lignosulfonate, and sodium stearate.

Cationic surfactants include benzalkonium chloride (BAC), cetylpyridinium chloride (CPC), Benzethonium chloride (BZT), cetyl trimethylammonium bromide (CTAB), and cetyl trimethylammonium chloride (CTAC).

Amphoteric surfactants include lauryl betain, betaine citrate, sodium lauroamphoacetate, sodium hydroxymethylglycinate, (carboxymethyl)dimethyl-3-[(1-oxododecyl)amino]propylammonium hydroxide, rennin, coco alkyldimethyl betaines, (carboxymethyl)dimethyloleylammonium hydroxide, cocoamidopropyl betaine, and (carboxylatomethyl)dimethyl(octadecyl)ammonium.

The surfactant can be a nonionic surfactant. In particular, the surfactant includes sorbitan monooleate or polysorbate 80. The surfactant may include two or more surfactants. In particular, the surfactant includes sorbitan monooleate and polysorbate 80.

The surfactant and LAC can be derived from a common plant type. An example common plant type for the LAC is *Cannabis sativa*. In an example a surfactant for the LAC is hemp protein.

Surfactants can also be characterized by the hydrophilic-lipophilic balance (HLB) which is the balance of the size and strength of the hydrophilic and lipophilic moieties of a surfactant molecule ranging from 0 to 20. Lower values are more hydrophobic and higher numbers are more hydrophilic. Anti-foaming agents may have an HLB of 1.5-3, water-in-oil emulsifiers have an HLB of 3-6, wetting agents have an HLB of 7-9, oil-in-water emulsifiers have an HLB of 8-12, and solubilizers have an HLB of 15-20. The surfactant may have an HLB value greater than 4, 5, 6, 7, 8, 9, 10, 11, 12, 13, 14, 15, 16, 17, 18, 19, or 20. In other embodiments, the surfactant has an HLB value between 4-6, 5-9, 8-17, 9-16.7, 9-16, 9-15, 9-14, 10-17, 10-16.7, 10-16, 10-15, 14-16, 14-17, 15-17, and between 10-14. In certain examples, the surfactant or plurality of surfactants can be chosen according to the HLB requirement of the LAC.

The aqueous formulations may include surfactant in an amount selected from: less than 20% w/w, less than 19% w/w, less than 18% w/w, less than 17% w/w, less than 16% w/w, less than 15% w/w, less than 14% w/w, less than 13% w/w, less than 12% w/w, less than 11% w/w, less than 10% w/w, less than 9% w/w, less than 8% w/w, less than 7% w/w, less than 6% w/w, or less than 5% w/w wherein the aqueous formulation includes at least 0.001% w/w surfactant.

The aqueous formulations may include surfactant in an amount selected from: 0.001% w/w to 1% w/w, 0.001% w/w to 2% w/w, 0.001% w/w to 3% w/w, 0.001% w/w to 4% w/w, 0.001% w/w to 5% w/w, 0.001% w/w to 6% w/w, 0.001% w/w to 7% w/w, 0.001% w/w to 8% w/w, 0.001% w/w to 9% w/w, or 0.001% w/w to 10% w/w surfactant.

A stabilizing agent is a substance that impacts rheology that is often added to an emulsion to increase viscosity to enhance the effectiveness of the product where it is applied. Stabilizing agents act as thickening or gelling agents that increase the viscosity of the final product.

In an embodiment the aqueous formulation further comprises a stabilizing agent.

In an embodiment the aqueous formulation has a stabilizing agent where the stabilizing agent is xanthan gum, locust bean gum, guar gum, konjac gum, gum arabic, ghatti gum, hydroxyethyl cellulose, carboxymethyl cellulose, alginates, kappa-carrageenan, lambda-carrageenan, iota-carrageenan, pectin, beta-lactoglobulin, whey protein, polyelectrolites, starch, modified starch, galactomannans, curdlan, gellan gum, carob gum, cellulose, gelatin, pectin, high methoxyl pectin, low methoxyl pectin, or any combinations thereof.

A weighting agent is a material that increases density. Weighting materials are added to emulsions to match the density of the binder to that of the vehicle. Phase separation of emulsion systems is prevented through density matching of the two phases.

In some embodiments the aqueous formulation further comprises a weighting agent.

In some embodiments the aqueous formulation has a weighting agent where the lipophilic weighting agent is sucrose acetate isobutyrate, brominated vegetable oil, ester gum, damar gum, octenyl succinate anhydride esters, or any combinations thereof.

A LAC refers to a compound that has the ability to dissolve in lipids and non-polar solvents and has an intended physiological effect in the body. A lipophilic active ingredient is a subset of LAC. Lipophilic active ingredients also have an intended physiological effect in the body but are also subject to government approval by a regulatory body, such as the U.S. Food & Drug Agency (FDA). LAC has an affinity for lipids. Lipophilic components generally include oils, fatty esters, hydrocarbon oils, silicones, waxes, fatty alcohols, lipophilic vitamins, and phospholipids. Within the context of the current disclosure, hydrophobic fluorocarbons are considered lipophilic components.

The present disclosure includes a LAC that may be naturally occurring in plants. A LAC that is naturally-occurring in plants means that the LAC can be found in a plant but does mean that the LAC originates from any plant. For example, the LAC can be extracted from the plant or the LAC can be synthetically produced. LAC may be artificial meaning that they are compounds that can be synthesized but do not otherwise exist in the natural environment.

Many families of plants exist, each including several species of plants. Exemplary species within plant families are provided below, and lipophilic components can be derived from each of them.

Acanthaceae: *Acanthus mollis; Justicia adhatoda.*

Actinidiaceae: *Actinidia chinensis; Actinidia deliciosa; Actinidia* sp.

Adoxaceae: *Sambucus canadensis; Sambucus chinensis; Sambucus edulus; Sambucus nigra; Sambucus sieboldiana; Sambucus* sp.; *Viburnum lantana; Viburnum opulus; Viburnum rhytidophyllum; Viburnum* sp.; *Viburnum tinus.*

Aizoaceae: *Mesembryanthemum crystallinum.*

Alstroemeriaceae: *Alstroemeria* sp.

Amaranthaceae: *Alternanthera* sp.; *Amaranthus blitum; Amaranthus caudatus; Amaranthus graecizans; Amaranthus hybridus; Amaranthus mangostanus; Amaranthus palmeri; Amaranthus retroflexus; Amaranthus* sp.; *Amaranthus spinosus; Amaranthus viridis; Atriplex canescens; Atriplex lentiformis; Atriplex semibaccata; Beta vulgaris; Celosia argentea; Chenopodium album; Chenopodium murale; Chenopodium* sp.; *Dysphania ambrosioides; Haloxylon ammodendron; Iresine herbstii; Salsola vermiculata; Spinacia oleracea.*

Amaryllidaceae: *Allium ampeloprasum; Allium cepa; Allium fistulosum; Allium sativum; Allium* sp.; *Narcissus* sp.

Anacardiaceae: *Mangifera indica; Pistacia terebinthus; Pistacia vera.*

Annonaceae: *Annona muricata; Annona reticulata; Annona squamosa.*

Apiaceae: *Aegopodium podagraria; Ammi majus; Apium graveolens; Apium nodiflorum; Arracacia xanthorrhiza; Athamanta macedonica; Bupleurum lancifolium; Coriandrum sativum; Cryptotaenia canadensis; Daucus carota; Eryngium* sp.; *Foeniculum vulgare; Pastinaca sativa; Petroselinum crispum; Peucedanum japonicum; Phellolophium madagascariense; Spananthe* sp.

Apocynaceae: *Ampelamus laevis; Apocynum cannabinum; Asclepias* sp.; *Catharanthus roseus; Mandevilla* sp.; *Matelea carolinensis; Nerium oleander; Plumeria* sp.; *Raphionacme* sp.; *Rauvolfia serpentina; Vinca major; Vinca* sp.

Aquifoliaceae: *Ilex crenata.*

Araceae: *Alocasia macrorrhizos; Alocasia* sp.; *Anthurium* sp.; *Arum italicum; Arum* sp.; *Caladium bicolor; Caladium* sp.; *Calla* sp.; *Colocasia esculenta; Colocasia* sp.; *Dieffenbachia* sp.; *Epipremnum pinnatum; Philodendron* sp.; *Symplocarpus foetidus; Xanthosoma* sp.; *Zantedeschia aethiopica.*

Araliaceae: *Aralia* sp.; *Hedera canariensis; Hedera helix; Hedera* sp.; *Hydrocotyle umbellata; Polyscias balfouriana; Schejflera actinophylla; Schejflera elegantissima; Schejflera* sp.; *Tetrapanax papyrifer.*

Araucariaceae: *Agathis* sp.; *Araucaria* sp.

Arecaceae: *Dypsis* sp.; *Phoenix dactylifera; Phoenix* sp.; *Veitchia* sp.

Aristolochiaceae: *Aristolochia clematitis.*

Asparagaceae: *Asparagus laricinus; Asparagus officinalis; Asparagus setaceus; Asparagus* sp.; *Aspidistra elatior; Cordyline fruticosa; Cordyline* sp.; *Dracaena braunii; Dracaena fragrans; Dracaena goldieana; Dracaena* sp.; *Hyacinthus orientalis; Eachenalia ensifolia; Maianthemum racemosum; Ornithogalum* sp.; *Polygonatum odoratum; Ruscus aculeatus; Yucca* sp.

Balsaminaceae: *Impatiens balsamina; Impatiens* sp.; *Impatiens walleriana.*

Berberidaceae: *Berberis cretica; Berberis thunbergii; Berberis vulgaris; Berberis wilsoniae; Nandina domestica.*

Betulaceae: *Alnus incana; Betula maximowicziana; Betula papyrifera; Betula pendula; Carpinus* sp.; *Corylus avellana.*

Bignoniaceae: *Campsis radicans; Pyrostegia venusta; Tecoma capensis; Tecoma stans. Boraginaceae: Borago officinalis; Cynoglossum columnae; Heliotropium arborescens; Heliotropium eichwaldii; Heliotropium europaeum; Nama hispidum; Omphalodes verna.*

Brassicaceae: *Aethionema saxatile; Brassica juncea; Brassica napus; Brassica oleracea; Brassica rapa; Brassica* sp.; *Capsella bursa-pastoris; Diplotaxis erucoides; Diplotaxis viminea; Eruca vesicaria; Erysimum graecum; Erysimum* sp.; *Erysimum* x *cheiri; Hirschfeldia incana; Eepidium didymum; Malcolmia* sp.; *Matthiola fruticulosa; Matthiola incana; Matthiola odoratissima; Nasturtium* sp.; *Raphanus raphanistrum; Raphanus* sp.; *Rapistrum rugosum; Rorippa indica; Sinapis arvensis; Zilla spinosa.*

Bromeliaceae: *Tillandsia* sp.

Buxaceae: *Buxus sempervirens.*

Calophyllaceae: *Mammea americana.*

Campanulaceae: *Campanula erinus; Lobelia* sp.; *Platycodon grandifloras.*

Cannabaceae: *Cannabis sativa; Cannabis indica; Cannabis ruderalis; Celtis australis; Celtis occidentalis; Humulus lupulus; americanus; Humulus cordifolius; Humulus neomexicanus; Humulus pubescens; Humulus scandens; Trema micrantha.*

Cannaceae: *Canna indica.*

Capparaceae: *Capparis nummularia.*

Caprifoliaceae: *Cephalaria gigantea; Diervilla* sp.; *Leycesteria formosa; Lonicera etrusca; Lonicera nigra; Lonicera periclymenum; Lonicera* sp.; *Lonicera tatarica; Lonicera xylosteum; Pterocephalus plumosus; Scabiosa sicula; Symphoria racemosa; Symphoricarpos albus; Symphoricarpos orbiculatus; Weigela hortensis.*

Caricaceae: *Carica papaya.*

Caryophyllaceae: *Dianthus armeria; Dianthus barbatus; Dianthus caryophyllus; Dianthus chinensis; Dianthus* sp.; *Dianthus tenuiflorus; Drymaria cordata; Gypsophila paniculata; Myosoton aquaticum; Silene chalcedonica; Silene vulgaris; Stellaria media.*

Celastraceae: *Celastrus orbiculatus; Celastrus scandens; Euonymus europaeus; Euonymus japonicus; Euonymus* sp.

Cistaceae: *Helianthemum salicifolium. Cleomaceae: Cleome* sp.; *Cleome viscosa.*

Clethraceae: *Clethra arborea.*

Combretaceae: *Terminalia catappa.*

Commelinaceae: *Commelina benghalensis; Commelina communis; Commelina diffusa.*

Compositae: *Acanthospermum hispidum; Achillea filipendulina; Achillea fraasii; Ageratum conyzoides; Ageratum houstonianum; Ambrosia trifida; Anthemis chia; Arctium lappa; Arctium minus; Arctotheca calendula; Arctotis* sp.; *Artemisia dracunculus; Beilis annua; Bidens bipinnata; Bidens biternata; Bidens pilosa; Bidens* sp.; *Boltonia* sp.; *Brachyscome* sp.; *Calendula arvensis; Calendula officinalis; Calendula* sp.; *Callistephus chinensis; Carduus crispus; Carthamus tinctorius; Centaurea cyanus; Centaurea hyalolepis; Centaurea iberica; Centaurea imperialis; Centaurea montana; Chaenactis stevioides; Chrysanthemum coronarium; Chrysanthemum indicum; Chrysanthemum morifolium; Chrysanthemum segetum; Chrysanthemum* sp.; *Chrysothamnus viscidiflorus; Cichorium endivia; Cichorium intybus; Cichorium pumilum; Cichorium spinosum; Conyza bonariensis; Conyza canadensis; Conyza* sp.; *Cosmos bipinnatus; Cosmos* sp.; *Crassocephalum crepidioides; Crepis neglecta; Crepis rubra; Cynara cardunculus; Cynara* sp.; *Dahlia coccinea; Dahlia* sp.; *Dahlia variabilis; Elephantopus mollis; Erigeron annuus; Erigeron* sp.; *Euryops* sp.; *Euthamia graminifolia; Galinsoga cara-* casana; Galinsoga ciliata; Galinsoga parviflora; Gerbera jamesonii; Gerbera sp.; Helianthella quinquenervis; Helianthus annuus; Helichrysum luteoalbum; Helichrysum tenax; Helichrysum thianschanicum; Heliopsis sp.; Helminthotheca echioides; Lactuca saligna; Lactuca sativa; Lactuca serriola; Eapsana communis; Eeontodon autumnalis; Eeucanthemum vulgare; Melampodium perfoliatum; Melanthera aspera; Mikania micrantha; Montanoa bipinnatifida; Notobasis syriaca; Osteospermum sp.; Parthenium sp.; Pentzia globosa; Picris pauciflora; Picris sprengeriana; Pseudo gnaphalium obtusifolium; Rudbeckia amplexicaulis; Rudbeckia sp.; Schkuhria pinnata; Scolymus maculatus; Scorzonera sp.; Senecio lividus; Senecio sp.; Senecio vulgaris; Solidago gigantea; Sonchus arvensis; Sonchus asper; Sonchus oleraceus; Sonchus sp.; Tagetes erecta; Tagetes microglossa; Tagetes minuta; Tagetes patula; Tagetes sp.; Taraxacum officinale; Tithonia rotundifolia; Tragopogon dubius; Tragopogon pratensis; Tridax procumbens; Urospermum dalechampii; Vernonia sp.; Xanthium strumarium; Zinnia elegans; Zinnia sp.

Convolvulaceae: *Calystegia hederacea; Calystegia sepium; Convolvulaceae* sp.; *Convolvulus arvensis; Convolvulus hirsutus; Convolvulus scammonia; Convolvulus siculus; Convolvulus* sp.; *Convolvulus tricolor; Dinetus racemosus; Ipomoea aquatica; Ipomoea arachnosperma; Ipomoea batatas; Ipomoea biflora; Ipomoea cairica; Ipomoea hochstetteri; Ipomoea indica; Ipomoea lacunosa; Ipomoea lobata; Ipomoea nil; Ipomoea purpurea; Ipomoea* sp.; *Ipomoea tricolor; Ipomoea triloba.*

Cornaceae: *Cornus alba; Cornus canadensis; Cornus nuttallii; Cornus* sp.

Cucurbitaceae: *Benincasa hispida; Bryonia alba; Citrullus colocynthis; Citrullus lanatus; Cucumis melo; Cucumis sativus; Cucumis* sp.; *Cucurbita ficifolia; Cucurbita maxima; Cucurbita moschata; Cucurbita pepo; Cucurbita* sp.; *Cucurbitaceae* sp.; *Diplocyclos palmatus; Ecballium elaterium; Lagenaria siceraria; Luffa acutangula; Luff a cylindrica; Momordica charantia; Praecitrullus fistulosus; Sechium edule.*

Cupressaceae: *Chamaecyparis thyoides; Cupressus* sp.; *Juniperus arizonica; Juniperus virginiana; Platycladus orientalis.*

Cyperaceae: *Cyperus esculentus; Cyperus rotundus; Cyperus schimperianus.*

Dipterocarpaceae: *Shorea robusta.*

Ebenaceae: *Diospyros kaki; Diospyros scabrida.*

Elaeagnaceae: *Elaeagnus angustifolia; Elaeagnus umbellata.*

Equisetaceae: *Equisetum palustre.*

Ericaceae: *Azalea nudiflora; Azalea* sp.; *Rhododendron* sp.; *Siphonandra* sp.

Euphorbiaceae: *Acalypha australis; Acalypha havanensis; Acalypha* sp.; *Acalypha wilkesiana; Codiaeum* sp.; *Codiaeum variegatum; Croton niveus; Croton* sp.; *Euphorbia amygdaloides; Euphorbia burmanni; Euphorbia helenae; Euphorbia helioscopia; Euphorbia hirta; Euphorbia hypericifolia; Euphorbia parviflora; Euphorbia pulcherrima; Euphorbia* sp.; *Hevea brasiliensis; Hura crepitans; Jatropha gossypiifolia; Jatropha hastata; Jatropha multifida; Jatropha* sp.; *Manihot esculenta; Manihot* sp.; *Mercurialis annua; Mercurialis* sp.; *Ricinus communis.*

Fagaceae: *Quercus alba; Quercus robur; Quercus* sp. *Garryaceae: Aucuba japonica.*

Gentianaceae: *Eustoma grandiflorum; Gentiana* sp.

Geraniaceae: *Erodium alnifolium; Geranium carolinianum; Geranium dissectum; Geranium lucidum; Geranium molle; Geranium rotundifolium; Geranium* sp.; *Pelargonium inquinans; Pelargonium* sp.

Gesneriaceae: *Saintpaulia ionantha.*

Goodeniaceae: *Goodenia* sp.; *Scaevola* sp.

Heliconiaceae: *Heliconia bihai; Heliconia latispatha.*

Hydrangeaceae: *Deutzia* sp.; *Hydrangea macrophylla; Hydrangea paniculata; Hydrangea* sp.; *Philadelphus coronarius; Philadelphus sericanthus.*

Iridaceae: *Crocosmia* x *crocosmiiflora; Gladiolus hortulanus; Gladiolus italicus; Gladiolus* sp.; *Iris sanguine* a; *Iris* x *germanica; Ixiaflexuosa.*

Juglandaceae: *Carya illinoinensis; Juglans regia; Juglans* sp.

Lamiaceae: *Ajuga* sp.; *Ballota africana; Clerodendrum chinense; Clerodendrum thomsoniae; Galeopsis speciosa; Galeopsis tetrahit; Glechoma hederacea; Glechoma* sp.; *Holmskioldia sanguine a; Holmskioldia* sp.; *Eamium album; Lamium amplexicaule; Eamium purpureum; Eamium* sp.; *Lavandula* sp.; *Leonotis ocymifolia; Leucas martinicensis; Marrubium vulgare; Melissa officinalis; Mentha arvensis; Mentha* sp.; *Mentha spicata; Mentha* x *piperita; Moluccella laevis; Monarda fistulosa; Nepeta cataria; Ocimum basilicum; Ocimum tenuiflorum; Perilla frutescens; Rosmarinus officinalis; Salvia argentea; Salvia officinalis; Salvia pratensis; Salvia* sp.; *Salvia splendens; Salvia verticillata; Salvia viridis; Stachys arvensis; Vitex negundo.*

Lauraceae: *Cassytha* sp.; *Endlicheria paniculata; Laurus nobilis; Persea americana.*

Leguminosae: *Acacia greggii; Acacia horrida; Acacia huarango; Acacia karroo; Acacia robusta; Acacia* sp.; *Alysicarpus longifolius; Amphicarpaea bracteata; Anthyllis vulneraria; Arachis hypogaea; Arachis* sp.; *Astragalus sinicus; Bauhinia forficata; Bauhinia monandra; Bauhinia* sp.; *Bauhinia variegata; Bituminaria bituminosa; Canavalia ensiformis; Caragana arborescens; Cassia artemisioides; Ceratonia siliqua; Cercis siliquastrum; Cicer arietinum; Clianthus* sp.; *Clitoria ternatea; Coronilla valentina; Crotalaria juncea; Crotalaria micans; Crotalaria* sp.; *Dalbergia sissoo; Dalea mollis; Desmodium khasianum; Dolichos* sp.; *Erythrina corallodendron; Erythrina poeppigiana; Erythrina* sp.; *Genista* sp.; *Gleditsia* sp.; *Glycine max; Indigofera arrecta; Indigofera holubii; Indigofera tinctoria; Inga* sp.; *Kennedia coccinea; Eablab purpureus; Laburnum anagyroides; Laburnum* sp.; *Lathyrus cicera; Lathyrus odoratus; Lathyrus sativus; Lens culinaris; Lespedeza maximowiczii; Lotus corniculatus; Lupinus arboreus; Lupinus argenteus; Lupinus sativus; Macroptilium atropurpureum; Macroptilium lathyroides; Medicago arabica; Medicago arborea; Medicago lupulina; Medicago orbicularis; Medicago polymorpha; Medicago sativa; Medicago* sp.; *Melilotus albus; Melilotus indicus; Melilotus* sp.; *Mucuna membranacea; Mucuna pruriens; Neonotonia wightii; Neorautanenia mitis; Onobrychis viciifolia; Ornithopus* sp.; *Phaseolus acutifolius; Phaseolus coccineus; Phaseolus lunatus; Phaseolus* sp.; *Phaseolus vulgaris; Pisum sativum; Psophocarpus tetragonolobus; Pueraria montana; Pueraria phaseoloides; Rhynchosia capitata; Rhynchosia caribaea; Robinia hispida; Robinia pseudoacacia; Sesbania cannabina; Sesbania herbacea; Spartium junceum; Styphnolobium japonicum; Teramnus uncinatus; Tipuana tipu; Trifolium alexandrinum; Trifolium aureum; Trifolium dasyurum; Trifolium dubium; Trifolium glome ratum; Trifolium hybridum; Trifolium incarnatum; Trifolium pratense; Trifolium purpureum; Trifolium repens; Trifolium* sp.; *Trifolium spumosum; Vicia angustifolia; Vicia faba; Vicia pulchella; Vicia sativa; Vicia* sp.; *Vicia villosa; Vigna aconitifolia; Vigna*

*angularis; Vigna mungo; Vigna radiata; Vigna* sp.; *Vigna unguiculata; Wisteria floribunda; Wisteria polystachya; Wisteria sinensis.*

Liliaceae: *Lilium* sp.

Linaceae: *Reinwardtia tetragyna.*

Lythraceae: *Cuphea* sp.; *Lagerstroemia speciosa; Punica granatum.*

Magnoliaceae: *Magnolia liliiflora; Magnolia* sp.; *Magnolia stellata.*

Malvaceae: *Abelmoschus esculentus; Abutilon pictum; Abutilon reflexum; Abutilon* sp.; *Abutilon theophrasti; Abutilon tubulosum; Alcea rosea; Althaea nudiflora; Byttneria australis; Ceiba pentandra; Corchorus capsularis; Corchorus olitorius; Gossypium barbadense; Gossypium herbaceum; Gossypium hirsutum; Gossypium* sp.; *Grewia asiatica; Grewia biloba; Helicteres guazumifolia; Hibiscus lunariifolius; Hibiscus mutabilis; Hibiscus rosa-sinensis; Hibiscus* sp.; *Hibiscus syriacus; Hibiscus trionum; Malva aegyptia; Malva moschata; Malva neglecta; Malva nicaeensis; Malva parviflora; Malva* sp.; *Malva sylvestris; Malva trimestris; Malvella leprosa; Sida rhombifolia; Sida* sp.; *Sterculia murex; Tilia americana; Tilia cordata; Tilia platyphyllos; Tilia rubra; Tilia* sp.; *Tilia tomentosa; Tilia* x *euchlora; Triumfetta semitriloba; Waltheria indica.*

Marantaceae: *Calathea* sp.; *Maranta* sp.

Meliaceae: *Azadirachta indica; Melia azedarach; Toona ciliata.*

Menispermaceae: *Tinospora fragosa.*

Moraceae: *Artocarpus altilis; Ficus carica; Ficus elastica; Ficus religiosa; Ficus* sp.; *Morus alba; Morus nigra; Morus rubra; Morus* sp.

Moringaceae: *Moringa oleifera.*

Musaceae: *Musa acuminata; Musa basjoo; Musa* sp.; *Musa* x *paradisiaca.*

Myrtaceae: *Eucalyptus grandis; Psidium cattleianum; Psidium guajava; Syzygium cumini.*

Nothofagaceae: *Nothofagus alpina.*

Nyctaginaceae: *Bougainvillea spectabilis.*

Olacaceae: *Ximenia americana.*

Oleaceae: *Forsythia koreana; Forsythia suspensa; Forsythia* x *intermedia; Fraxinus angustifolia; Fraxinus excelsior; Fraxinus ornus; Fraxinus* sp.; *Jasminum humile; Jasminum nudiflorum; Jasminum officinale; Jasminum sambac; Jasminum* sp.; *Ligustrum lucidum; Ligustrum vulgare; Olea europaea; Osmanthus fragrans; Syringa oblata; Syringa vulgaris.*

Onagraceae: *Chylismia claviformis; Epilobium angustifolium; Fuchsia magellanica; Fuchsia* sp.; *Fuchsia* x *hybrida; Gaura* sp.; *Oenothera biennis; Oenothera laciniata; Oenothera* sp.; *Oenothera tetraptera.*

Orchidaceae: *Catasetum* sp.; *Cymbidium* sp.; *Orchidaceae* sp.; *Papilionanthe teres. Oxalidaceae: Oxalis corniculata; Oxalis debilis; Oxalis europaea; Oxalis floribunda; Oxalis* sp.

Papaveraceae: *Argemone mexicana; Bocconia frutescens; Chelidonium majus; Chelidonium* sp.; *Dicentra* sp.; *Eschscholzia* sp.; *Fumaria officinalis; Papaver aculeatum; Papaver nudicaule; Papaver orientale; Papaver rhoeas; Papaver somniferum.*

Passifloraceae: *Passiflora caerulea; Passiflora edulis; Passiflora foetida; Passiflora mollissima; Passiflora* sp.

Paulo wniaceae: *Paulownia fortunei.*

Pedaliaceae: *Sesamum indicum.*

Phyllanthaceae: *Phyllanthus amarus; Phyllanthus* sp.

Phytolaccaceae: *Petiveria alliacea; Phytolacca americana; Phytolacca dioica; Phytolacca esculenta; Phytolacca icosandra.*

Pinaceae: *Pinus sylvestris; Tsuga canadensis.*

Pittosporaceae: *Pittosporum tobira.*

Plantaginaceae: *Angelonia* sp.; *Antirrhinum majus; Digitalis purpurea; Hippuris vulgaris; Linaria genistifolia; Mecardonia procumbens; Plantago asiatica; Plantago lanceolata; Plantago major; Plantago* sp.; *Veronica persica; Veronica* sp.; *Veronica teucrium.*

Platanaceae: *Platanus orientalis; Platanus* sp.

Plumbaginaceae: *Limoniastru guyonianum; Limonium sinuatum; Plumbago auriculata; Plumbago* sp.

Poaceae: *Aegilops* sp.; *Agropyron desertorum; Aira* sp.; *Avena fatua; Avena sativa; Avenasp.; Avena sterilis; Bambusa* sp.; *Bromus catharticus; Bromus* sp.; *Chondrosum barbatum; Cynodon dactylon; Dactyloctenium aegyptium; Digitaria argillacea; Digitaria ciliaris; Digitaria diversinervis; Digitaria sanguinalis; Eleusine coracana; Elymus hispidus; Elymus repens; Eragrostis* sp.; *Festuca arundinacea; Festuca* sp.; *Helictotrichon pratense; Hordeum* sp.; *Lolium multiflorum; Lolium* sp.; *Ophiuros exaltatus; Oryza glaberrima; Oryza sativa; Panicum miliaceum; Panicum* sp.; *Paspalum dilatatum; Pennisetum clandestinum; Pennisetum purpureum; Phleum pratense; Poa annua; Poa pratensis; Poa trivialis; Poaceae* sp.; *Rottboellia cochinchinensis; Saccharum officinarum; Setaria pumila; Setaria viridis; Sitanion hystrix; Sorghum bicolor; Sorghum halepense; Sorghum* sp.; *Stenotaphrum secundatum; Triticum* sp.; *Zea mays; Zeugites* sp.

Polemoniaceae: *Phlox Carolina; Phlox paniculata; Phlox* sp.

Polygonaceae: *Emex australis; Fallopia baldschuanica; Fallopia convolvulus; Persicaria hydropiper; Persicaria longiseta; Persicaria maculosa; Persicaria pensylvanica; Polygonum argyrocoleon; Polygonum aviculare; Rumex acetosa; Rumex acetosella; Rumex crispus; Rumex japonicus; Rumex obtusifolius; Rumex* sp.

Pontederiaceae: *Eichhornia crassipes.*

Portulacaceae: *Portulaca oleracea.*

Primulaceae: *Cyclamen graecum; Cyclamen hederifolium; Cyclamen persicum; Cyclamen* sp.; *Primula denticulata; Primula polyantha; Primula* sp.; *Primula veris.*

Ranunculaceae: *Adonis aestivalis; Anemone coronaria; Anemone hortensis; Aquilegia* sp.; *Clematis paniculata; Clematis* sp.; *Delphinium* sp.; *Helleborus* sp.; *Ranunculus asiaticus; Thalictrum fendleri.*

Resedaceae: *Reseda odorata.*

Rhamnaceae: *Frangula dodonei; Helinus integrifolius; Rhamnus alpina; Rhamnus imeretina; Ziziphus jujuba; Ziziphus spina-christi.*

Rosaceae: *Alchemilla vulgaris; Armeniaca mume; Cerasus lusitanica; Cerasus serrula; Cerasus vulgaris; Chaenomeles japonica; Chaenomeles sinensis; Cotoneaster horizontalis; Cotoneaster microphyllus; Cotoneaster tomentosa; Crataegus laevigata; Crataegus monogyna; Crataegus sanguinea; Cydonia oblonga; Eriobotrya japonica; Filipendula ulmaria; Fragaria moschata; Fragaria vesca; Fragaria virginiana; Fragaria* x *ananassa; Geum rivale; Malus domestica; Malus floribunda; Malus pumila; Malus* sp.; *Marcetella maderensis; Padus avium; Potentilla fragarioides; Potentilla fruticosa; Potentilla norvegica; Potentilla tanacetifolia; Prunus amygdalus; Prunus armeniaca; Prunus avium; Prunus cerasifera; Prunus cerasoides; Prunus cerasus; Prunus domestica; Prunus insititia; Prunus lusitanica; Prunus persica; Prunus salicina; Prunus serotina; Prunus* sp.; *Prunus spinosa; Pyracantha coccinea; Pyracantha koidzumii; Pyracantha* sp.; *Pyrus communis; Pyrus pyrifolia; Pyrus* sp.; *Rosa canina; Rosa cymosa; Rosa hybrida; Rosa multiflora; Rosa odorata; Rosa rugosa; Rosa* sp.; *Rosa* x *alba; Rosa* x *centifolia; Rosa* x *damascena; Rosa* x *rugosa; Rubus buergeri; Rubus chaerophyllus; Rubus chingii; Rubus fruticosus; Rubus idaeus; Rubus lloydianus; Rubus occidentalis; Rubus* sp.; *Rubus ulmifolius; Sorbus aucuparia; Sorbus* sp.; *Spiraea japonica.*

Rubiaceae: *Coffea arabica; Coffea abbayesii; Coffea affinis; Coffea alleizettii; Coffea ambanjensis; Coffea ambongenis; Coffea andrambovatensis; Coffea ankaranensis; Coffea anthonyi; Coffea arenesiana; Coffea augagneurii; Coffea bakossii; Coffea benghalensis; Coffea bertrandii; Coffea betamponensis; Coffea bissetiae; Coffea boinensis; Coffea boiviniana; Coffea bonnieri; Coffea brassii; Coffea brevipes; Coffea bridsoniae; Coffea buxifolia; Coffea canephora; Coffea carrissoi; Coffea charrieriana; Coffea cochinchinensis; Coffea commersoniana; Coffea congensis; Coffea costatifructa; Coffea coursiana; Coffea dactylifera; Coffea decaryana; Coffea dubardii; Coffea ebracteolata; Coffea eugenioides; Coffea fadenii; Coffea farafanganensis; Coffea floresiana; Coffea fotsoana; Coffea fragilis; Coffea fragrans; Coffea gallienii; Coffea grevei; Coffea heimii; Coffea homollei; Coffea horsfieldiana; Coffea humbertii; Coffea humblotiana; Coffea humilis; Coffea jumellei; Coffea kapakata; Coffea kianjavatensis; Coffea kihansiensis; Coffea kimbozensis; Coffea kivuensis; Coffea labatii; Coffea lancifolia; Coffea lebruniana; Coffea leonimontana; Coffea leroyi; Coffea liaudii; Coffea liberica; Coffea ligustroides; Coffea littoralis; Coffea lulandoensis; Coffea mabesae; Coffea macrocarpa; Coffea madurensis; Coffea magnistipula; Coffea malabarica; Coffea mangoroensis; Coffea mannii; Coffea manombensis; Coffea mapiana; Coffea mauritiana; Coffea mayombensis; Coffea mcphersonii; Coffea melanocarpa; Coffea merguensis; Coffea millotii; Coffea minutiflora; Coffea mogenetii; Coffea mongensis; Coffea montekupensis; Coffea montis-sacri; Coffea moratii; Coffea mufindiensis; Coffea myrtifolia; Coffea namorokensis; Coffea neobridsoniae; Coffea neoleroyi; Coffea perrieri; Coffea pervilleana; Coffea pocsii; Coffea pseudozanguebariae; Coffea pterocarpan; Coffea racemose; Coffea rakotonasoloi; Coffea ratsimamangae; Coffea resinosa; Coffea rhamnifolia; Coffea richardii; Coffea sahafaryensis; Coffea sakarahae; Coffea salvatrix; Coffea sambavensis; Coffea sapinii; Coffea schliebenii; Coffea semsei; Coffea sessiliflora; Coffea stenophylla; Coffea tetragona; Coffea togoensis; Coffea toshii; Coffea travancorensis; Coffea tricalysioides; Coffea tsirananae; Coffea vatovavyensis; Coffea vavateninensis; Coffea vianneyi; Coffea vohemarensis; Coffea wightiana; Coffea zanguebariae; Galium aparine; Galium stellatum; Gardenia jasminoides; Gardenia* sp.

Rutaceae: *Choisya ternata; Citrus aurantiifolia; Citrus aurantium; Citrus Clementina; Citrus limon; Citrus maxima; Citrus medica; Citrus paradisi; Citrus reticulata; Citrus sinensis; Citrus* sp.; *Citrus trifoliata; Ruta graveolens; Zanthoxylum rhoifolium.*

Salicaceae: *Dovyalis caffra; Populus alba; Populus nigra; Populus* sp.; *Populus tremula; Populus* x *canadensis; Salix aegyptiaca; Salix alba; Salix babylonica; Salix caprea; Salix chaenomeloides; Salix dephnoides; Salix fragilis; Salix* sp.; *Salix viminalis.*

Sapindaceae: *Acer campestre; Acer negundo; Acer platanoides; Acer pseudoplatanus; Acer rubrum; Acer saccharum; Acer* sp.; *Aesculus glabra; Dodonaea viscosa; Koelreuteria paniculata; Litchi sinensis; Sapindus* sp.

Saxifragaceae: *Rodgersia podophylla.*

Scrophulariaceae: *Buddleja davidii; Buddleja madagascariensis; Diascia* sp.; *Myoporum* sp.; *Nemesia* sp.; *Verbascum blattaria.*

Simaroubaceae: *Ailanthus altissima.*

Solanaceae: *Acnistus arborescens; Brugmansia arborea; Brugmansia suaveolens; Brugmansia* x *Candida; Calibrachoa* sp.; *Capsicum annuum; Capsicum* sp.; *Cestrum cyaneum; Cestrum elegans; Cestrum strigillatum; Cyphomandra* sp.; *Datura metel; Datura* sp.; *Datura stramonium; Lycium chinense; Nicandra physalodes; Nicotiana glauca; Nicotiana* sp.; *Nicotiana tabacum; Petunia* sp.; *Petunia* x *hybrid; Physalis acutifolia; Physalis alkekengi; Physalis angulata; Physalis lagascae; Physalis peruviana; Salpichroa origanifolia; Solanum aethiopicum; Solanum americanum; Solanum capsicoides; Solanum carolinense; Solanum delagoense; Solanum elaeagnifolium; Solanum grandiflorum; Solanum laciniatum; Solanum lycopersicum; Solanum macrocarpon; Solanum mammosum; Solanum melongena; Solanum muricatum; Solanum nigrum; Solanum panduraeforme; Solanum quitoense; Solanum* sp.; *Solanum tuberosum; Withania somnifera.*

Strelitziaceae: *Strelitzia reginae.*

Theaceae: *Camellia japonica; Camellia sinensis; Camellia* sp.

Thymelaeaceae: *Dais cotinifolia.*

Tropaeolaceae: *Tropaeolum majus; Tropaeolum* sp.

Ulmaceae: *Ulmus americana; Ulmus glabra; Ulmus laevis; Ulmus pumila; Ulmus rubra; Ulmus* sp.

Urticaceae: *Boehmeria nivea; Laportea aestuans; Parietaria judaica; Parietaria officinalis; Pipturus albidus; Urtica dioica; Urtica* sp.; *Urtica urens.*

Verbenaceae: *Aloysia citriodora; Duranta erecta; Glandularia phlogiflora; Lantana camara; Lippia alba; Verbena bracteata; Verbena brasiliensis; Verbena hybrida; Verbena officinalis; Verbena* sp.

Violaceae: *Viola odorata; Viola* sp.; *Viola tricolor; Viola* x *wittrockiana.*

Vitaceae: *Ampelopsis* sp.; *Parthenocissus quinquefolia; Parthenocissus tricuspidata; Vitis* sp.; *Vitis vinifera.*

Xanthorrhoeaceae: *Hemerocallis fulva; Hemerocallis minor.*

Zingiberaceae: *Curcuma longa; Zingiber mioga.*

Zygophyllaceae: *Tribulus terrestris.*

The LAC in this disclosure may be from a plant in the plant family Cannabaceae, Rubiaceae, and/or Theaceae.

The LAC in this disclosure may be from a plant in the Cannabaceae family, for example, from a *cannabis* plant including *Cannabis sativa, Cannabis indica*, and/or *Cannabis ruderalis.*

The LAC in this disclosure may be from a hops plant including a *Humulus* plant including *Humulus lupulus, Humulus japonicus, Humulus americanus, Humulus cordifolius, Humulus neomexicanus, Humulus pubescens*, and/or *Humulus scandens.*

The LAC in this disclosure may be from the Rubiaceae family and is a *Coffea* plant including *Coffea abbayesii, Coffea affinis, Coffea alleizettii, Coffea ambanjensis, Coffea ambongenis, Coffea andrambovatensis, Coffea ankaranensis, Coffea anthonyi, Coffea arabica, Coffea arenesiana, Coffea augagneurii, Coffea bakossii, Coffea benghalensis, Coffea bertrandii, Coffea betamponensis, Coffea bissetiae, Coffea boinensis, Coffea boiviniana, Coffea bonnieri, Coffea brassii, Coffea brevipes, Coffea bridsoniae, Coffea buxifolia, Coffea canephora, Coffea carrissoi, Coffea charrieriana, Coffea cochinchinensis, Coffea commersoniana, Coffea congensis, Coffea costatifructa, Coffea coursiana, Coffea dactylifera, Coffea decaryana, Coffea dubardii, Coffea bracteolatea, Coffea eugenioides, Coffea fadenii, Coffea farafanganensis, Coffea floresiana, Coffea fotsoana, Coffea fragilis, Coffea fragrans, Coffea gallienii, Coffea grevei, Coffea heimii, Coffea homollei, Coffea horsfieldiana, Coffea*

*humbertii, Coffea humblotiana, Coffea humilis, Coffea jumellei, Coffea kapakata, Coffea kianjavatensis, Coffea kihansiensis, Coffea kimbozensis, Coffea kivuensis, Coffea labatii, Coffea lancifolia, Coffea lebruniana, Coffea leonimontana, Coffea leroyi, Coffea liaudii, Coffea liberica, Coffea ligustroides, Coffea littoralis, Coffea lulandoensis, Coffea mabesae, Coffea macrocarpa, Coffea madurensis, Coffea magnistipula, Coffea malabarica, Coffea mangoroensis, Coffea mannii, Coffea manombensis, Coffea mapiana, Coffea mauritiana, Coffea mayombensis, Coffea mcphersonii, Coffea melanocarpa, Coffea merguensis, Coffea millotii, Coffea minutiflora, Coffea mogenetii, Coffea mongensis, Coffea montekupensis, Coffea montis-sacri, Coffea moratii, Coffea mufindiensis, Coffea myrtifolia, Coffea namorokensis, Coffea neobridsoniae, Coffea neoleroyi, Coffea perrieri, Coffea pervilleana, Coffea pocsii, Coffea pseudozanguebariae, Coffea pterocarpan, Coffea racemose, Coffea rakotonasoloi, Coffea ratsimamangae, Coffea resinosa, Coffea rhamnifolia, Coffea richardii, Coffea sahafaryensis, Coffea sakarahae, Coffea salvatrix, Coffea sambavensis, Coffea sapinii, Coffea schliebenii, Coffea semsei, Coffea sessiliflora, Coffea stenophylla, Coffea tetragona, Coffea togoensis, Coffea toshii, Coffea travancorensis, Coffea tricalysioides, Coffea tsirananae, Coffea vatovavyensis, Coffea vavateninensis, Coffea vianneyi, Coffea vohemarensis, Coffea wightiana*, and/or *Coffea zanguebariae.*

The LAC in this disclosure may be from the Theaceae family and is a tea plant including *Camellia sinensis*. The variants of *Camellia sinensis* include *Camellia sinensis* var. *sinensis, Camellia sinensis* var. *assamica, Camellia sinensis* var. *pubilimba*, or *Camellia sinensis* var. *dehungensis*. Some example tea varieties include black tea, green tea, white tea, oolong tea, pu-erh tea, and purple tea which are all made from the *Camellia sinensis* tea plant. *Camellia sinensis* var. *sinensis* grows primarily in China and other East Asian countries and has a milder, mellower character, and *Camellia sinensis* var. *assamica* grows primarily in India and is generally heartier and more robust. Other varieties include *Camellia sinensis* var. *pubilimba* and *Camellia sinensis*. var. *dehungensis.*

The LAC in this disclosure may be from the Zingiberaceae family and is a turmeric plant including *Curcuma longa.*

A LAC may be a first LAC that is chosen for an intended physiological effect (e.g., the first LAC is an active compound or an active ingredient). A first LAC may include a cannabinoid; alpha-acids (e.g., humulone, cohumulone, adhumulone, posthumulone, prehumulone, adprehumulone) beta-acids (e.g., lupulone, colupuloe, adlupulone, prelupulone, postlupulone), or flavonoids (e.g., xanthohumol, or xanthan humulone) from a hops plant; tryptophan alkaloids or diterpenes from a coffee plant; resveratrol, or proanthocyanidins from a tea plant; or coenzyme Q10 (ubiquinone or ubiquinol), plastoquinone, plastoquinonol, or other fat-soluble electron transport chain components found in the mitochondria of plants (and all respiring eukaryotic cells).

The LAC in this disclosure may be from multiple plant types. For example, resveratrol can be found in tea but can also be found in peanuts, grapes, wine, and soy.

As used herein, the term "cannabinoid" is generally understood to include any chemical compound that acts upon a cannabinoid receptor. For instance, cannabinoids may include endocannabinoids (i.e., produced naturally by humans and animals), phytocannabinoids (i.e., found in cannabis and some other plants), and artificial cannabinoids (i.e., manufactured and not naturally occurring).

The cannabinoid in the aqueous formulation can be a naturally derived cannabinoid, a synthetically modified cannabinoid from a natural cannabinoid, a synthetic cannabinoid, a cannabinoid that is modified by action of the atmosphere, an endocannabinoid, or any combination thereof.

In some embodiments the aqueous formulation the cannabinoid can be tetrahydrocannabinolic acid (THCA), delta-9-tetrahydrocannabinol (delta-9-THC), cannabidiol acid (CBDA), cannabidiol (CBD), delta-8-tetrahydrocannabinol (delta-8-THC), cannabinol (CBN), cannabichromene (CBC), cannabidivarin (CBDV), cannabigerolic acid (CBGA), cannabigerol (CBG), cannabicyclol (CBL), tetrahydrocannabivarin (THCV), tetrahydrocannabiphorol (THCP), dexanabinol (HU-211), 1,1-dimethylheptyl-11-hydroxy-tetrahydreannabinol (HU-210), 1-pentyl-3-(4-methoxybenzoyl)indole (RCS-4), cannabicyclohexanol (CP 47,497), cannabipiperidiethanone (CPE), N-(1-adamantyl)-1-pentyl-1H-indole-3-carboxamide (APICA), AZD-1940, 1-pentyl-3-(2-methoxyphenylacetyl)indole (JWH-250), JWH-051, JWH-176, AB-FUBINACA, AB-FUBINACA, CUMYL-CBMICA, FUB-PB-22, THJ-2201, JWH-203, 5F,AB-FUPPYCA, WIN 55,202-2, PB-22, FAB-144, UR-144, anandamide (AEA), 2-arachidonoyl glycerol (2-AG), 1-(2-cyclohexylethyl)-3-(2-methoxyphenylacetyl) indole (RS-8), 1-pentyl-3-(4-methoxybenzoyl)indole (RSC-4), (1-pentyl-3-(1-naphthoyl)indole (JWH-018), or any combination thereof.

Examples of cannabinoids include cannabidiol (CBD), cannabigerolic acid (CBGA), cannabigerol (CBG), cannabigerol monomethylether (CBGM), cannabigerovarin (CBGV), cannabichromene (CBC), cannabichromevarin (CBCV), cannabidiol monomethylether (CBDM), cannabidiol-C4 (CBD-C4), cannabidivarin (CBDV), cannabidiorcol (CBD-C1), delta-9-tetrahydrocannabinol (A9-THC), delta-9-tetrahydrocannabinolic acid A (THCA-A), delta-9-tetrahydrocannabionolic acid B (THCA-B), delta-9-tetrahydrocannabinolic acid-C4 (THCA-C4), delta-9-tetrahydrocannabinol-C4, delta-9-tetrahydrocannabivarin (THCV), delta-9-tetrahydrocannabiorcol (THC-C1), delta-7-cis-iso tetrahydrocannabivarin, delta-8-tetrahydrocannabinol (delta-8-THC), cannabicyclol (CBL), cannabicyclovarin (CBLV), cannabielsoin (CBE), cannabinol (CBN), cannabinol methylether (CBNM), cannabinol-C4 (CBN-C4), cannabivarin (CBV), cannabinol-C2 (CBN-C2), cannabiorcol (CBN-C1), cannabinodiol (CBND), cannabinodivarin (CBVD), cannabitriol (CBT), 10-ethoxy-9-hydroxy-delta-6a-tetrahydrocannabinol, 8,9-dihydroxy-delta-6a-tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-delta-6a-tetrahydrocannabionol (OTHC), delta-9-cis-tetrahydrocannabinol (cis-THC), 3,4,5,6-tetrahydro-7-hydroxy-alpha,alpha,2-trimethyl-9-n-propyl-2,6-methano-2H-1-benzoxocin-5-methanol (OH-iso-HHCV), cannabiripsol (CBR), trihydroxy-delta-9-tetrahydrocannabinol (triOHTHC), cannabinol propyl variant (CBNV), cannabidiolic acid (CBDA), cannabitriol (CBO), and tetrahydrocannabivarinic acid (THCVA) and derivatives thereof. Further examples of cannabinoids are discussed in PCT Patent Application Pub. No. WO2017/190249 and U.S. Patent Application Pub. No. US2014/0271940.

The term "derivative" in chemistry refers to a compound that is obtained from a similar compound or a precursor compound by a chemical reaction.

Examples of cannabinoids that can be synthetically produced include: naphthoylindoles, naphthylmethylindoles, naphthoylpyrroles, naphthylmethylindenes, phenylacetylindoles, cyclohexylphenols, tetramethylcyclopropylindoles, adamantoylindoles, indazole carboxamides, and quinolinyl esters. Derivatives of natural cannabinoids can include metabolites of cannabinoids. For example, the metabolite of CBD includes 7-OH-CBD and the metabolite of CBDV includes 7-OH-CBDV. Examples of cannabinoids include 3-carbamoyl-2-pyridone, and its derivatives and/or analogs; pyrimidine derivatives and/or analogs; carenadiol and its derivatives and/or analogs; cannabinoid carboxylic acids and their derivatives and/or analogs; pyrido[3,2-E][1,2,4]triazolo[4,3-C]pyrimidine and its derivatives and/or analogs; tetrahydro-pyrazolo[3,4-C]pyridine and its derivatives and/or analogs; bicyclo[3.1.1]heptan-2-one cannabinoid and its derivatives and/or analogs; resorcinol and its derivatives and/or analogs; dexanabinol compounds and their derivatives and/or analogs; cannabimimetic lipid amide compounds and their derivatives and/or analogs; nabilone and its derivatives and/or analogs; 2-oxoquinolone compounds and their derivatives and/or analogs; and 3,4-diaryl-4,5-dihydro-(h)-pyrazole-1-carboxamide and its derivatives and/or analogs.

Cannabinoid derivatives may include, 3-carbamoyl-2-pyridone and its derivatives and/or analogs include methyl 3-methyl-2-{[2-oxo-1-(2-oxo-ethyl)-1,2,5,6,7,8,9,10-octahydrocycloocta[b]pyridine-3-carbonyl]-amino}-butyrate; dimethyl 2-[(1-cyclohexylmethyl-5,6-dimethyl-2-oxo-1,2-dihydropyridine-3-carbonyl)-amino]-succinate; and methyl 2-{[1-(3-methoxycarbonyamino-propyl)-2-oxo-1,2,5,6,7,8,9,10octahydrocycloocta[b]pyridine-3-carbonyl]-amino}-2-methyl-propionate. Pyrimidine derivatives such as Formula (I) (2-((2,4-dichlorophenyl)amino)-N-((tetrahydro-2H-pyran-4-yl)methyl)-4-(trifluoromethyl)pyrimidine-5-carboxamide) as shown below

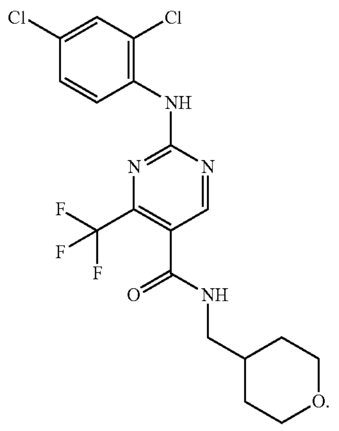 [SMILES: O=C(NCC1CCOCC1)c1cnc(Nc2ccc(Cl)cc2Cl)nc1C(F)(F)F]

Other pyrimidine derivatives and/or analogs include 2-(3-chlorophenylamino)-4-trifluoromethylpyrimidine-5-carboxylic acid cyclohexylmethyl-amide; 2-phenylamino-4-trifluoromethylpyrimidine-5-carboxylic acid cyclohexylmethyl-amide; 1-[2-(2,3-dichlorophenylamino)-4-trifluoromethylpyrimidin-5-yl]-1-morphol-in-4-yl-methanone; 1-[2-(2,4-dichlorophenylamino)-4-trifluoromethylpyrimidin-5-yl]-1-morphol-in-4-yl-methanone; and 2-(3-chlorophenylamino)-4-trifluoromethylpyrimidin-5-carboxylic acid cyclopentylamide. Carenadiol and its derivatives can be used and/or analogs include compounds having Formula (II) as shown below wherein R is a lower alkyl having 1 to 9 carbon atoms including isomeric forms such as i-butyl, n-butyl, t-butyl, $C_5H_{11}$ or 1,1-dimethylheptyl.

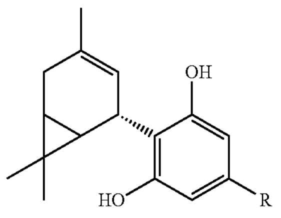

Cannabinoid carboxylic acids and their derivatives and/or analogs include compounds such as CBDA (Formula III), THCA-A (Formula IV), THCA-B Formula (V), and CBGA (Formula VI) which are shown below. These types of compounds can have a straight-chain, branched or cyclic hydrocarbon residue with one C atom to 12 C atoms; and salts can include NH4+, mono-, di- or trivalent metal ions; or primary, secondary, tertiary or quaternary organic ammonium ions with up to 48 C atoms, which may bear still further functional groups.

CBDA

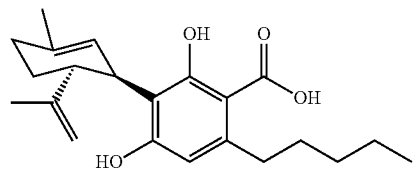

CBGA

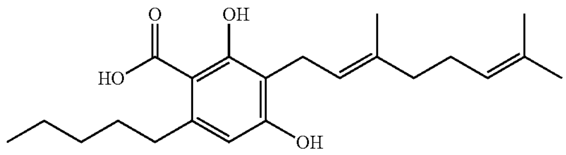

THCA-A

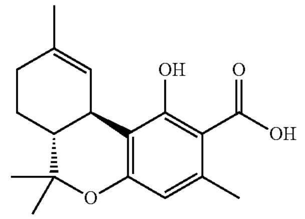

THCA-B

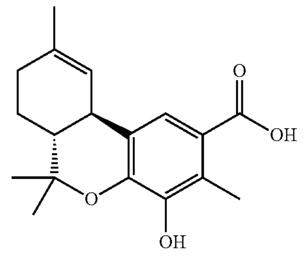

Examples of multivalent ammonium ions include N,N-dicyclohexylamine-H+ and N,N-dicyclohexyl-N-ethylamine-H+. X+ can also be the hydrogen cation of a physiologically active substance with at least one basic nitrogen atom, such as for example morphine, methadone (or an enantiomer thereof) or hydromorphone.

Further cannabinoid derivative examples include pyrido [3,2-E][1,2,4]triazolo[4,3-C]pyrimidine and its derivatives and/or analogs include 5-tert-butyl-8-(2-chlorophenyl)-9-(4-chlorophenyl)pyrido[3,2-e][1,2,4]triazolo[4,3-c]pyrimidin-3(2H)-one; 8-(4-bromo-2-chlorophenyl)-5-tert-butyl-9-(4-chlorophenyl)pyrido[3,2-e][1,2,4]triazolo[4,3-c]pyrimidin-3(2H)-one; 5-fert-butyl-9-(4-chlorophenyl)-8-(2-methylphenyl)pyrido[3,2-e][1,2,4]triazolo[4,3-c]pyrimidin-3(2H)-one; 9-(4-bromophenyl)-5-tert-butyl-8-(2-chlorophenyl)pyrido[3,2-e][1,2,4]triazolo[4,3-c]pyrimidin-3(2H)-one; and 5-tert-butyl-8-(2-chlorophenyl)-9-(4-chlorophenyl)pyrido[3,2-e][1,2,4]triazolo[4,3-c]pyrimidine.

Tetrahydro-pyrazolo[3,4-C]pyridine and its analogs and/or derivatives include compounds having Formula (VII), (VIII), (IX), (X), or (XI) as shown below Formula (VII)

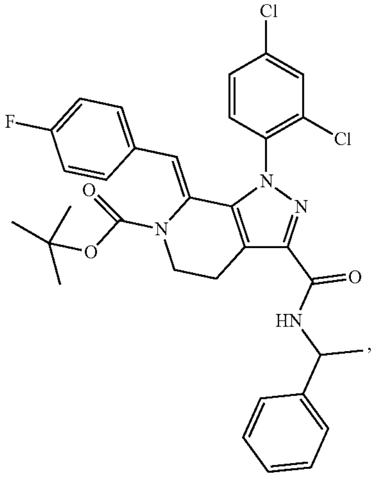

Formula (VIII)

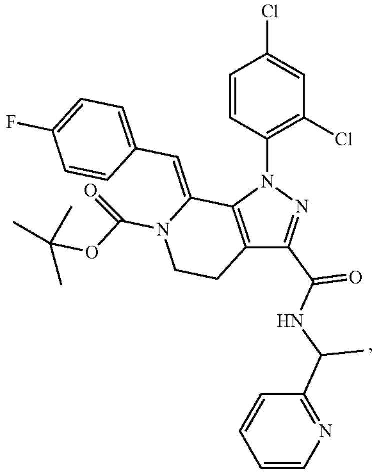

-continued

Formula (IX)

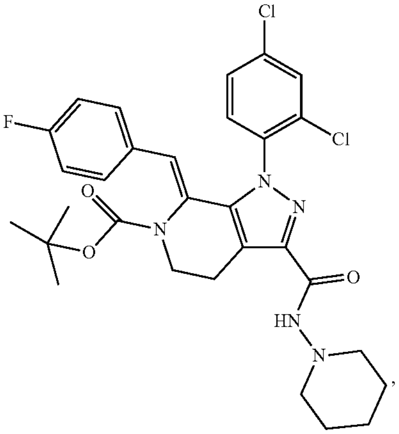

Formula (X)

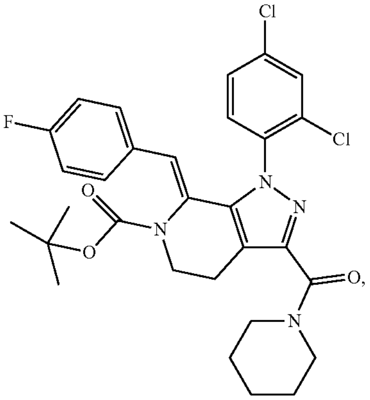

or

Formula (XI)

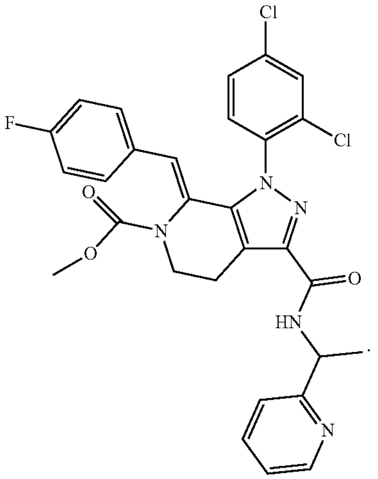

Bicyclo[3.1.1]heptan-2-one cannabinoids and their derivatives and/or analogs include compounds having a structure as shown below

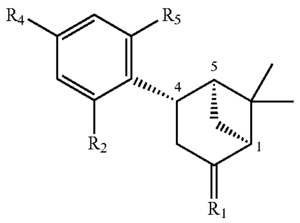

having a specific stereochemistry wherein C-4 is S, the protons at C-1 and C-5 are cis in relation to one another and the protons at C-4 and C-5 are trans; and wherein: $R_1$ is (a) O or S; (b) $C(R')_2$ wherein R' at each occurrence is independently selected from the group consisting of hydrogen, cyano, —OR", —$N(R")_2$, a saturated or unsaturated, linear or branched C1-C6 alkyl, C1-C6 alkyl-OR" or C1-C6alkyl-$N(R")_2$ wherein at each occurrence R" is independently selected from the group consisting of hydrogen, C(O)R'", C(O)$N(R'")_2$, C(S)R'", saturated or unsaturated, linear or branched C1-C6 alkyl, C1-C6 alkyl-OR'", and C1-C6 alkyl-$N(R'")_2$, wherein at each occurrence R'" is independently selected from the group consisting of hydrogen or saturated or unsaturated, linear, branched or cyclic C1-C12 alkyl; or (c) NR" or N—OR" wherein R" is as previously defined; $R_2$ and $R_3$ are each independently (a) —R", —OR", —$N(R")_2$, —SR", —S(O)(O)NR", wherein at each occurrence R" is as previously defined; (b) —S(O)Rb, —S(O)(O)$R_b$, wherein $R_b$ is selected from the group consisting of hydrogen, saturated or unsaturated, linear or branched C1-C6 alkyl, C1-C6 alkyl-OR", and C1-C6 alkyl-$N(R")_2$, wherein R" is as previously defined; or (c) —OC(O)OH, —OS(O)(O)$OR_e$, —OP(O)$(OR_e)_2$, —$OR_d$ or —OC(O)—$R_d$ chain terminated by —C(O)OH, —S(O)(O)$OR_e$, or —P(O)$(OR_e)_2$, wherein $R_d$ is a saturated or unsaturated, linear or branched C1-C6 alkyl and Re is at each occurrence selected from the group consisting of hydrogen and $R_d$ as previously defined; and $R_4$ is (a) R wherein R is selected from the group consisting of hydrogen, halogen, OR'", OC(O)R", C(O)OR'", C(O)R'", OC(O)OR'", CN, $N(R'")_2$, NC(O)R'", NC(O)OR'", C(O)N$(R'")_2$, NC(O)$N(R'")_2$, and SR'", wherein at each occurrence R'" is as previously defined; (b) a saturated or unsaturated, linear, branched or cyclic C1-C12 alkyl-R wherein R is as previously defined; (c) an aromatic ring which can be further substituted at any position by R wherein R is as previously defined; or (d) a saturated or unsaturated, linear, branched or cyclic C1-C12 alkyl optionally terminated by an aromatic ring which can be further substituted as defined in (c).

Resorcinol and its derivatives and/or analogs may include compounds having a structure as shown below where $R_1$ is (a) straight or branched alkyl chain of 7 to 12 carbon atoms; (b) —O—$R_3$, where $R_3$ is a straight or branched alkyl chain of 5 to 9 carbon atoms, optionally substituted by one phenyl group; or (c) —$(CH_2)_n$—O—$R_4$, where n is an integer from 1 to 7, and $R_4$ is a straight alkyl chain of 1 to 5 carbon atoms; and $R_2$ is a non-cyclic terpenoid including from 10 to 30 carbon atoms.

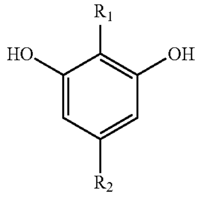

Resorcinol and derivatives

Resorcinol and its derivatives and/or analogs can include compounds having as shown above wherein $R_1$ and $R_2$ are as follows: $R_1$ is a straight alkyl chain of 5 to 8 carbon atoms, optionally substituted with one methyl group; and $R_2$ is selected from geranyl optionally substituted with one —OH, and farnesyl optionally substituted with one —OH.

Resorcinol and its derivatives and/or analogs may include compounds having a structure as shown above wherein: $R_1$ is (a) straight or branched alkyl chain of 7 to 12 carbon atoms; (b) —O—$R_3$, where $R_3$ is a straight or branched alkyl chain of 5 to 9 carbon atoms, optionally substituted by one phenyl group; or (c) —$(CH_2)_n$—O—$R_4$, where n is an integer from 1 to 7, and $R_4$ is a straight alkyl chain of 1 to 5 carbon atoms; and $R_2$ is a non-cyclic terpenoid including from 10 to 30 carbon atoms; with the proviso that when $R_1$ is isononyl, $R_2$ is not geranyl.

Resorcinol and its derivatives and/or analogs can include compounds having a structure as shown above wherein $R_1$ is (a) a straight or branched alkyl of 7 to 12 carbon atoms; (b) a group —O—$R_3$, where $R_3$ is a straight or branched alkyl of 5 to 9 carbon atoms, or a straight or branched alkyl substituted at the terminal carbon atom by a phenyl group; or (c) a group —$(CH_2)_n$—O-alkyl, where n is an integer from 1 to 7 and the alkyl group contains 1 to 5 carbon atoms.

Resorcinol and its derivatives and/or analogs may include compounds of a structure as shown above wherein $R_2$ is a non-cyclic terpenoid carbon chain such as geranyl, farnesyl, and related non-cyclic terpenes and their isomers as well as other non-cyclic paraffinic or olefinic carbon chains.

Resorcinol and its derivatives and/or analogs may include compounds of the structure shown above wherein $R_1$ is dimethylheptyl and $R_2$ is geranyl.

Dexanabinol compounds and their derivatives and/or analogs may include high enantiomeric purity compounds having a structure as shown below and having the (3S, 4S) configuration and being in enantiomeric excess of at least 99.90% over the (3R,4R) enantiomer.

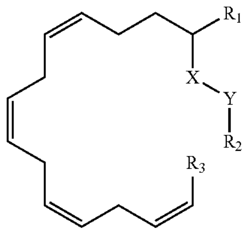

Cannabimimetic Lipid Amide compounds

Cannabimimetic lipid amide compounds and their derivatives and/or analogs may include compounds as shown above where X is one of the group consisting of C═O and NH, and Y is the other of that group. Expressed another way, X may be C═O and Y may be NH, or Y may be C═O and X may be NH, but both X and Y may not be the same group. $R_1$ is H or an alkyl group. Variants of cannabimimetic lipid amide compounds shown above include $R_1$ is H, $CH_3$, or $(CH_3)_2$; $R_2$ is an alkyl, a substituted alkyl, an alkenyl or an alkynyl group. In other derivatives $R_2$ is CH(R) $CH_2Z$, $CH_2CH(R)Z$, or $CH(R)(CH_2)_nCH_2Z$; R being H, CH, $CH_3$, CHCH, $CH_2CF_3$, or $(CH_3)_2$; Z being H, halogen, $N_3$, NCS, or OH; and n being selected from the group consisting of 0, 1 and 2. $R_3$ is an alkyl, a substituted alkyl, an aryl, an alkylaryl, an O-alkyl, an O-alkylaryl, a cyclic and a heterocyclic group. O-alkyl and O-alkylaryl refer to groups in which an oxygen atom is interposed between carbon atoms on the anandamide portion and substituent group. Examples of such $R_3$ groups include cyclohexyl, cyclopentyl, alkylcyclohexyl, alkylcyclopentyl, piperidinyl, morpholinyl and pyridinyl. In some derivative examples $R_3$ is n-$C_5H_{10}Z'$, n-$C6H_{12}Z'$, n-$C7H_{14}Z'$, or 1', 1'-$C(CH_3)_2(CH_2)_5$ $CH_2Z'$; Z' being H, halogens, CN, $N_3$, NCS, or OH.

Cannabimimetic lipid amide compounds and their derivatives and/or analogs may include compounds as shown below

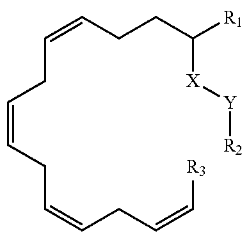

Cannabimimetic Lipid Amide compounds where Y is one of the group consisting of C═O and NH and X is the other of that group. $R_1$ is H or an alkyl group. Variants of the molecule shown above include $R_1$ is H, $CH_3$, or $(CH_3)_2$. $R_2$ is an alkyl, a substituted alkyl, an alkenyl, an alkynyl, an O-alkyl, a cyclic, a polycyclic, or a heterocyclic group. Variants of the above structure include $R_2$ being as shown below

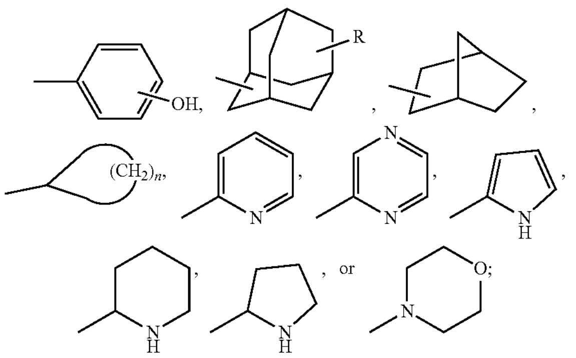

and further CH═$CH_2$, CH═$C(CH_3)_2$, C≡CH, $CH_2OCH_3$, $CH(R)(CH_2)_nCH_2Z$, or $CH_2CH(R)(CH_2)_nZ$; R being H, $CH_3$ or $(CH_3)_2$; Z being H, halogens, $N_3$, NCS, OH, or OAc; and n 0, 1, or 2; and $R_3$ is an alkyl, a substituted alkyl, an aryl, an alkylaryl, an O-alkyl, an O-alkylaryl, a cyclic, or a heterocyclic group. In certain derivatives $R_3$ includes cyclohexyl, cyclopentyl, alkylcyclohexyl, alkylcyclopentyl, piperidinyl, morpholinyl and pyridinyl. In certain derivatives $R_3$ is n-$C5H_{10}Z'$, n-$C6H_{12}Z'$, n-$C7H_{14}Z'$, or 1',1'-$C(CH_3)_2$ $CH_2)_5$ $CH_2Z'$; Z' being H, halogen, CN, $N_3$, NCS, or OH.

Nabilone and its derivatives and/or analogs may include compounds as shown below where $R_1$-$R_{36}$ are independently selected from the group consisting of hydrogen and deuterium. Nabilone derivatives and/or analogs can refer to compounds wherein at least one of $R_1$-$R_{36}$ includes deuterium.

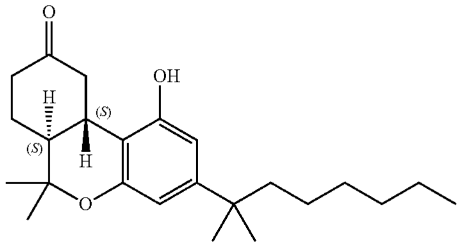

Nabilone

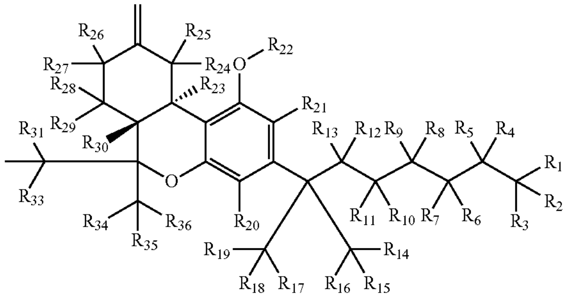

Nabilone Derivatives

Cannabinoids can be considered a class of active pharmaceutical ingredients or API's. Thus, it would be natural for one skilled in the art to substitute an API in lieu of a cannabinoid in any aspect of the presented disclosure. An active ingredient is any ingredient that provides biologically active or other direct effect in the diagnosis, cure, mitigation, treatment, or prevention of disease or to affect the structure or any function of the body of humans or animals. An API can affect either the human or animal physically or mentally. APIs can include synthetic or manmade compounds, naturally occurring compounds, and herbal compounds. Medicines fall under API's. Aqueous formulations of the present disclosure can be formulated into a pharmaceutical formulation. Pharmaceutical formulations include any formulation (e.g., formulations described above) when the formulation is subject to government approval by a regulatory agency, such as the U.S. FDA.

In some embodiments the aqueous formulation has an active pharmaceutical agent that is used in lieu of a cannabinoid.

In some embodiments of the aqueous formulation the active pharmaceutical agent has a bioavailability of about 10% to about 65%.

In some embodiments the aqueous formulation the active pharmaceutical agent that is used can be acetaminophen, paracetamol, cetirizine, levocetirizine, loratadine, ibuprofen, naproxen, dextromethorphan, salicylic acid, acetylsalicylic acid, Revlimid, Apremilast, sildenafil, tadalafil, or vardenafil.

Further API's that can be used for this disclosure may be Adalimumab, Apixaban, Dulaglutide, Semaglutide, Ustekinumab, Insulin glargine Pembrolizumab, Bictegravir/emtricitabine/tenofovir, Alafenamide, Etanercept, Empagliflozin, Rivaroxaban, Sitagliptin, Insulin aspart, Insulin lispro, Dupilumab, Immune globulin, Secukinumab, Liraglutide, Epinephrine, Nivolumab, Ibrutinib, Budesonide/formoterol, Ocrelizumab, Lisdexamfetamine, Lurasidone, Remdesivir, Pembrolizumab, Immune globulin, Alteplase, Vasopressin, Rituximab, Tocilizumab Inactivated influenza virus, Natalizumab, Nivolumab, Ocrelizumab, Bictegravir/emtricitabine/tenofovir alafenamide, Pegfilgrastim, Infliximab, Sugammadex, Denosumab, Immunoglobulin, antithymocyte, Iohexol, Bupivacaine, Albumin. Adalimumab, Bevacizumab, Vedolizumab, Piperacillin/tazobactam, or Daratumumab/hyaluronidase.

A first LAC from the *Humulus* plant may include: alpha-acids (e.g., humulone, cohumulone, adhumulone, posthumulone, prehumulone, adprehumulone) beta-acids (e.g., lupulone, colupuloe, adlupulone, prelupulone, postlupulone), from a hops plant; terpenes, sesquiterpenoids, diterpenoids, and triterpenoids, phytoestrogens, and flavonoids (e.g., xanthan humulone or xanthohumol).

A first LAC from a *Coffea* plant may include: tryptophan alkaloids, diterpenes, linoleic acid, palmitic acid, triacylglycerols, diterpene esters, triterpene esters, and triterpenes.

A first LAC from a *Camellia* plant may include: resveratrol, proanthocyanidins, terpenoid esters, diacylglycerol, sterol esters, and beta-amyrin esters.

A first LAC from a plant may include coenzyme Q10, plastoquinone, plastoquinonol, or other fat-soluble electron transport chain components found in the mitochondria of plants (and all respiring eukaryotic cells). Ubiquinone and ubiquinol are example forms of coenzyme Q10.

Aqueous formulations disclosed herein can include more than one LAC. At least one of the LAC is provided as an active compound or an active ingredient. When more than one LAC is used, the additional lipophilic component(s) can also be active compounds or active ingredients, and/or can be provided as carriers.

Additional lipophilic components may include a second lipophilic component or additional lipophilic components may include a second LAC and a third LAC. Furthermore, additional lipophilic components may include a second LAC, a third LAC, and a fourth LAC leading to additional lipophilic components including 1, 2, 3, 4, 5, 6, 7, 8, 9, or 10 additional LAC. The additional lipophilic components may include a terpene, essential oil, alkaloid, a linoleic acid, a palmitic acid, a triacylglycerol, a terpene ester, a terpenoid ester, a diacylglycerol, a sterol ester, a beta-amyrin ester, a carrier oil, or any of the first LAC described earlier.

In an embodiment the aqueous formulation is presented, wherein the LAC further comprises additional lipophilic component or combinations of additional lipophilic components.

In an embodiment the aqueous formulation is presented, wherein the additional lipophilic component or combinations of additional lipophilic components are from about 0.01 wt. % to 99 wt. % of the LAC.

In an embodiment the aqueous formulation is presented, wherein the additional lipophilic component or combinations of additional lipophilic components are oils, fatty esters, hydrocarbon oils, silicones, waxes, fatty alcohols, lipophilic vitamins, phospholipids, white/yellow paraffin, hard paraffin, microcrystalline wax, petrolatum, cholesterol, bees wax, spermaceti wax, plastibase, ceresin, or any combinations thereof.

In an embodiment the aqueous formulation is presented, wherein the oils are corn oil, castor oil, soybean oil, linseed oil, sunflower oil, safflower oil, canola coil, peanut oil, cacao butter, coconut oil, cotton seed oil, sesame oil, almond oil, hydrogenated sulphated castor oil, hempseed oil, medium chain triglycerides, monoglycerides, diglycerides, triglycerides, or any combinations thereof.

In an embodiment the aqueous formulation is presented, wherein the lipophilic vitamins are alpha-carotene, beta-carotene, gamma-carotene, delta-carotene, epsilon-carotene, lycopene, retinol, retinal, esters of retinol, a carotenoid, ergocalciferol, cholecalciferol, alpha-tocopherol, beta-tocopherol, gamma-tocopherol, delta-tocopherol, alpha-tocotrienol, beta-tocotrienol, gamma-tocotrienol, delta-tocotrienol, phylloquinone, phytonadione, menaquinone, menaphthone, menadione, anthocyanins, catechins, flavonoids, isoflavonoids, polyphenols, zoochemicals, xanthophylls, astaxanthin, cryptoxanthin, zeaxanthin, antheraxanthin, violaxanthin, diatoxanthin, lutein, neurosporene, phytol, isophytol, essential fatty acids, omega-3, omega-6, omega-9, or any combination thereof.

As used herein, a terpene refers to a hydrocarbon or derivative thereof, found as a natural product and biosynthesized by oligomerization of isoprene units (terpenes can also be synthetically produced). A terpene can be acyclic, monocyclic, bicyclic, or multicyclic. Examples include limonene, pulegone, caryophyllene epoxide, bisabalol and the like. As used herein, the term "terpene" includes corresponding terpenoid or sesquiterpenoid compounds. Over 100 different terpenes have been identified in the cannabis plant, and every strain tends toward a unique terpene type and composition. Examples of terpenes include: beta-caryophyllene [(1R,4E,9S)-4,11,11-trimethyl-8-methylene-bicyclo(7.2.0)undec-4-ene]; beta-caryophyllene oxide; citronellol [3,7-dimethyloct-6-en-1-ol]; alpha-eudesmol [2-[(2R,4aR)-4a,8-dimethyl-2,3,4,5,6,8a-hexahydro-1H-naphthalen-2-yl]propan-2-ol]; beta-eudesmol [2-[(2R,4aR,8aS)-4a-methyl-8-methylidenel,2,3,4,5,6,7,8a-octahydronaphthalen-2-yl]propan-2-ol]; gamma-eudesmol [2-[(2R,4aR)-4a,8-dimethyl-2,3,4,5,6,7-hexahydro-1H-naphthalen-2-yl]propan-2-ol]; geraniol [(2E)-3,7-dimethylocta-2,6-dien-1-ol]; guaiol [2-[(3S,5R,8S)-3,8-dimethyl-1,2,3,4,5,6,7,8-octahydroazulen-5-yl]propan-2-ol]; alpha-humulene [(1E,4E,8E)-2,6,6,9-tetramethylcycloundeca-1,4,8-triene]; beta-humulene [(1E,5E)-1,4,4-trimethyl-8-methylidenecycloundeca-1,5-diene]; gamma-humulene [(1Z,6E)-1,8,8-trimethyl-5-methy denecycloundeca-1,6-diene]; D-limonene [(4R)-1-methyl-4-prop-1-en-2-ylcyclohexene]; L-limonene [(4S)-1-methyl-4-prop-1-en-2-ylcyclohexene]; (−)-linalool [(3R)-3,7-dimethylocta-1.6-dien-3-ol]; (+)-linalool [(3S)-3,7-dimethylocta-1,6-dien-3-ol]; alpha-myrcene [2-methyl-delta-methybdeneocta-1,7-diene]; beta-myrcene [7-methyl-3-methylideneocta-1,6-diene]; nerol [(2Z)-3,7-dimethylocta-2,6-dien-1-ol]; cis-nerolidol [(6Z)-3,7,11-trimethyldodeca-1,6,10-trien-3-ol]; trans-nerolidol [(6E)-3,7,11-trimethyldodeca-1,6,10-trien-3-ol]; alpha-ocimene [(3E)-3,7-dimethylocta-1,3,7-triene]; beta-ocimene [(3E)-3,7-dimethylocta-1,3,6-triene]; p-cymene [1-methyl-4-(1-methylethyl)benzene]; alpha-phellandrene [2-methyl-5-propan-2-ylcyclohexa-1,3-diene]; beta-phellandrene [3-methybdene-delta-propan-2-ylcyclohexene]; cis-phytol [(Z,7R,11R)-3,7,11,15-tetramethylhexadec-2-en-1-ol]; trans-phytol [(E,7R,11R)-3,7,11,15-tetramethylhexadec-2-en-1-ol]; (−)-alpha-pinene [(1S,5S)-4.6.6-trimethylbicyclo[3.1.1]hept-3-ene]; (+)-alpha-pinene [(1R,5R)-4,6,6-trimethylbicyclo[3.1.1]hept-3-ene]; (+)-beta-pinene [(1R,5R)-6,6-dimethyl-4-methylidenebicyclo[3.1.1]heptane];

(−)-pulegone [(5S)-5-methyl-2-propan-2-yldenecyclohexan-1-one]; (+)-pulegone [(5R)-5-methyl-2-propan-2-ybdenecyclohexan-1-one]; alpha-terpinene [1-methyl-4-propan-2-ylcyclohexa-1,3-diene]; delta-terpinene [5-methyl-2-propan-2-ylcyclohexa-1,3-diene]; gamma-terpinene [1-methyl-4-propan-2-ylcyclohexa-1,4-diene]; alpha-terpineol [2-(4-methylcyclohex-3-en-1-yl)propan-2-ol]; gamma-terpineol [1-methyl-4-propan-2-ylidenecyclohexan-1-ol]; and (+)-valencene [(3R,4aS,5R)-4a,5-dimethyl-3-prop-1-en-2-yl-2,3,4,5,6,7-hexahydro-1H-naphthalene].

The aqueous formulations may include one or more terpenes selected from limonene and/or bisabolol. Terpenoids may include sesquiterpenoids, diterpenoids, or triterpenoids. A sesquiterpenoid includes, for example, isohumulone. Terpenes may include monoterpenes, sesquiterpenes, diterpenes, or triterpenes. The monoterpene may include limonene, myrcene, geraniol, linalool, terpineol, alpha-pinene, or beta-pinene. The sesquiterpene may include humulene, caryophyllene, or bisabolol. The triterpene may include squalene. The terpene ester may include a diterpene ester or a triterpene ester.

Examples of essential oils include alpha-pinene, beta-pinene, beta-myrcene, limonene, alpha-humulene, beta-farnesene, beta-caryophyllene, alpha-selinene, beta-selinene, and/or gamma-muurolene.

Additional lipophilic components may include an oil carrier. Oil carriers can include medium chain triglycerides (MCT) and/or long chain triglycerides. Oil carriers can also include borage oil, castor oil, coconut oil, cottonseed oil, soybean oil, safflower oil, sunflower oil, castor oil, corn oil, olive oil, palm oil, peanut oil, poppy seed oil, canola oil, hydrogenated soybean oil, hydrogenated vegetable oils, sesame oil, triolein, trilinolein, and trilinolenin.

The oil carrier can be olive oil and/or sesame oil, MCT fractionated from coconut oil, hemp oil, sunflower oil, olive oil, corn oil, or sesame oil, including mixtures thereof.

Additional lipophilic components or combinations of additional lipophilic components can be in the aqueous formulation at amounts ranging from 0.01% to 20% w/w. An example aqueous formulation can include a terpene or a combination of terpenes in an amount of 0.01% w/w, 0.5% w/w, 0.75% w/w, 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, or 20% w/w. Further additional lipophilic components or combinations of additional lipophilic components can be in the aqueous formulation at an amount of at least 0.5% w/w, at least 0.75% w/w, at least 1% w/w, at least 2% w/w, at least 3% w/w, at least 4% w/w, at least 5% w/w, at least 6% w/w, at least 7% w/w, at least 8% w/w, at least 9% w/w, at least 10% w/w, at least 11% w/w, at least 12% w/w, at least 13% w/w, at least 14% w/w, at least 15% w/w, at least 16% w/w, at least 17% w/w, at least 18% w/w, at least 19% w/w, or at least 20% w/w.

In particular, a ratio of first LAC to additional lipophilic component includes: 1:1, 1:2, 1:3, 1:4, 1:5, 1:6, 1:7, 1:8, 1:9, 1:10, 10:1, 9:1, 8:1, 7:1, 6:1, 5:1, 4:1, 3:1, 2:1, 5:4, 3:8, 9:2, 2:3, or 1:1.

In certain examples, LAC within an aqueous formulation is selected from the same plant type. For example, an aqueous formulation can include two LAC from a common plant type, three LAC from a common plant type, four LAC from a common plant type, five LAC from a common plant type, or six LAC from a common plant type. These embodiments provide aqueous formulations with a high concentration of ingredients from a common plant type. One certain example includes CBD and humulene. Other examples include a cannabinoid (e.g., CBD) in combination with alpha-tocopherol, beta-tocopherol, gamma-tocopherol, and/or delta-tocopherol). In these combinations, the tocopherols can provide a useful antioxidant function, preventing or reducing degradation of active components within an aqueous formulation. Other embodiments may combine particular components from different plant types, for example CBD from a cannabis plant and theanine from a tea plant.

Formulations include aqueous formulations as disclosed herein prepared for a particular use. During preparation for a use (i.e., formulation), the nature of an aqueous formulation may change so that it no longer meets the structural definitions or features provided herein. For example, LAC in an aqueous formulation may become substantially unevenly dispersed during a formulation process. The liquid portion of an aqueous media or liquid composition may evaporate during a formulation process, such that only LAC and other components remain. Alternatively, the liquid portion of an aqueous media may be purposefully removed to produce powdered or dehydrated versions of the LAC with glycosides and surfactant(s). Other changes, such as will be understood by one of ordinary skill in the formulation arts, may also occur.

Examples of formulations include beverages and beverage kits, consumer products, drops, gels, patches, films, sprays, foams, aerosols, sublingual capsules, tablets, suppositories, capsules, pessaries, tinctures, strips, lozenges, creams, lotions, balms, topicals, ointments, syrups, pastes, liquids, powders, solids, gas, inhalants, or rings, to name a few.

Aqueous formulations of the present disclosure can be formulated into a beverage or a beverage kit. A beverage is a liquid intended for consumption. A beverage kit includes a container including LAC and an aqueous formulation disclosed herein in a form to be added to a liquid for drinking. The form can be liquid, a dried powder, granules, syrups, concentrates, and the like. The kit can include the container including the LAC, aqueous formulation, and optionally can include a beverage that the contents of the container can be added to before drinking.

Examples of beverages include coffee, tea, beer, juice, milk (both dairy and non-dairy), water, liquor, punch, a shake, soda, cocoa beverages, energy drink, drinkable yogurt, fermented beverages, cider, popsicles, and wine.

Beverages and/or beverage kits may include flavoring agents, sweeteners, nutritional additives, preservatives, pH modifiers, coloring agents, taste-masking agents, viscosity modifiers, and thickeners.

Aqueous formulations of the present disclosure may be formulated into a food product. Food products generally are those that are chewed before swallowing.

For example, food products may be made by inclusion or infusion of LAC containing aqueous formulations of the present disclosure into a foodstuff. Food products may be made by combining LAC and aqueous formulations of the present disclosure with other ingredients to make an edible food product, including butters and oils. Exemplary oils include coconut oil, grape seed oil, olive oil, palm oil, papaya seed oil, peanut oil, sesame oil, sprouted wheat oil, wheat germ oil, or any combination thereof.

The LAC and aqueous formulations of the present disclosure can be added to the food product at any stage of its preparation. For example, the aqueous formulations can be mixed with the food product's ingredients so that it is distributed throughout the food product and the product may be cooked, or the aqueous formulations can be added to the final food product. The aqueous formulations of the present disclosure may be applied to the surface of the food product, e.g., as a glaze, icing, or coating.

Food products that the current disclosure is applicable to includes flavoring agents, sweeteners, nutritional additives, preservatives, pH modifiers, coloring agents, taste-masking agents, viscosity modifiers, and thickeners.

Aqueous formulations of the present disclosure can be formulated into an oral formulation. Oral formulations referred to herein are formulations that are delivered by the mouth that are not conventional beverages or food products and are not subject to a regulatory approval process.

Examples of oral formulations include syrups, gels, chewables, tinctures, and oils.

Oral formulations may include as part of the formulation preservatives, pH modifiers, coloring agents, taste-masking agents, viscosity modifiers, and thickeners.

Oral formulations can be manufactured using processes that are well known to those of skill in the art. Excipients include diluents, binders, disintegrants, dispersants, lubricants, glidants, stabilizers, surfactants and colorants.

Oral formulations can include additional active compounds or active ingredients and can be formulated with any compounds suitable for administration as an oral formulation. The oral formulation may include components that do not impair the desired action of the oral formulation and/or components that supplement the desired action of the oral formulation.

Aqueous formulations of the present disclosure can be formulated into a mucosal formulation.

Examples of mucosal formulations include nebulizers, ointments, creams, lotions, foams, sprays, mousses, pastes, gels, liquid droplets, and dissolvable films. Mucosal formulations referred to herein refer to formulations delivered through moist cavities such as the lining of the mouth (sublingual and buccal), bladder, rectal, genital, or nasal cavity. Mucosal formulations administered buccally can be formulated into sprays, gels, pastes, dissolvable tablets or dissolvable strips. Mucosal formulations administered sublingually can be formulated into lozenges, sprays, gels, pastes, dissolvable tablets or dissolvable strips. Mucosal formulations administered bronchially or pulmonary can be formulated into an aerosol, pressurized atomizers, inhalers of dry powder, or dissolved in volatile liquids. Mucosal formulations administered rectally can be formulated into suppositories, ointments, creams, suspensions, solutions, lotions, pastes, gels, sprays, foams or oils. Mucosal formulations administered vaginally can be formulated into suppositories, ointments, creams, suspensions, solutions, lotions, pastes, gels, sprays, foams or oils. Mucosal formulations administered nasally can be formulated into ointments, suspensions, solutions, lotions, pastes, gels, sprays or mists.

Mucosal formulations of the present disclosure can include preservatives, pH modifiers, coloring agents, taste-masking agents, film-forming polymers, penetration enhancers, viscosity modifiers, lubricants, and thickeners.

Mucosal formulations may include liquid droplets administered sublingually. Mucosal formulations include nebulizers, and such mucosal formulations may include a spray for administration nasally. Mucosal formulations may also include suppository types of administration.

Mucosal formulations often include a nebulizer. Nebulizers are broadly known to those of skill in the art and the invention is not limited to any type of nebulizer.

Common Considerations & Components for Drinkable, Ingestible, and/or Inhalable Products & Formulations. Flavoring agents useful herein include any material or mixture of materials operable to enhance the taste of a drinkable formulation. Any orally acceptable natural or synthetic flavoring agents can be used, such as essential oils, various flavoring aldehydes, flavoring oils, esters, alcohols, similar materials, as well as sweeteners such as sodium saccharin, xylitol, D-mannose, and combinations thereof. Essential oils can include: Ylang Ylang (*Cananga odorata*); Yarrow (*Achillea millefolium*); Violet (*Viola odorata*); Vetiver (*Vetiveria zizanoides*); Vanilla (*Vanilla plantifolia*); Tuberose (*Polianthes tuberosa*); Thyme (*Thymus vulgaris* L.); Tea Tree (*Melaleuca altemifolia*); Tangerine (*Citrus reticulata*); Spruce, Black (*Picea mariana*); Spruce (*Tsuga Canadensis*); Spikenard (*Nardostachys jatamansi*); Spearmint (*Mentha spicata*); Sandalwood (*Santalum spicatum*); Rosewood (*Aniba rosaeodora*); Rosemary Verbenone (*Rosmarinus officinalis*); Rosemary (*Rosmarinus officinalis*); Rose (*Rosa damascena*); Rose Geranium (*Pelargonium roseum*); *Ravensara* (*Ravensara aromatica*); Plai (*Zingiber cassumunar*) Pine Needle (*Pinus sylvestris* L.); Petitgrain (*Citrus aurantium*); Peppermint (*Mentha piperita*); Pepper, Black (*Piper nigrum* L.); Patchouli (*Pogostemon cablin*); Palo Santo (*Bursera graveolens*); Palmarosa (*Cymbopogon martini*); *Osmanthus* (*Osmanthus fragrans*); Oregano (*Origanum vulgare*); Orange, Sweet (*Citrus sinensis*); Oak Moss (*Evemia prunastri*); Nutmeg (*Myristica fragrans*) Niaouli (*Melaleuca viridifloria*); Neroli (aka Orange Blossom) (*Citrus aurantium*); Myrtle (*Myrtus communis*); Myrrh (*Commiphora myrrha*); *Mimosa* (*Acacia decurrens*); *Melissa* (*Melissa officinalis* L); Marjoram, Sweet (*Origanum majorana*); Manuka (*Leptospermum scoparium*); Mandarin, Red (*Citrus deliciosa*); Mandarin (*Citrus deliciosa*); Lotus, White (*Nelumbo nucifera*); Lotus, Pink (*Nelumbo nucifera*); Lotus, Blue (*Nelumbo nucifera*); Lime (*Citrus aurantifolia*); Lily (*Lilum aurantum*); Lemongrass (*Cymbopogon citratus*); Lemon (*Citrus limonum*); Lavender (*Lavandula angustifolium*); Lavandin (*Lavandula hybrida grosso*); Kanuka (*Kunzea ericoides*); Juniper Berry (*Juniperus cummunis*); Jasmine (*Jasminum officinale*); Jasmine Abs (*Jasminum sambac*); Helichr sum (*Helichrysum italicum*); Grapefruit, White (*Citrus* x *paradisi*); Grapefruit, Pink (*Citrus paradisi*); Ginger (*Zingiber officinalis*); Geranium (*Pelargonium graveolens*); Geranium, Bourbon (*Pelargonium graveolens*, 'Herit); *Gardenia* (*Gardenia jasminoides*); *Galbanum* (*Ferula galbaniflua*); Frankincense (*Boswellia carterii*); Frangipani (*Plumeria alba*); Fir Needle White (*Abies alba*); Fir Needle Siberia (*Abies sibenca*); Fir Needle Canada (*Abies balsamea*); Fennel, Sweet (*Foeniculum vulgare*); *Eucalyptus Smithii. Eucalyptus Radiata, Eucalyptus Globulus, Eucalyptus Citriodora, Eucalyptus* Blue Mallee (*Eucalyptus polybractea*); Elemi (*Canarium luzonicum*); Dill (*Anethum graveolens*); Cypress (*Cupressus sempervirens*); Cumin (*Cuminum cyminum*); Coriander (*Coriandum sativum*); Cocoa (*Theobroma cacao*); Clove (*Eugenia caryophylatta*); Clary Sage (*Salvia sclarea*); *Cistus* (aka Labdanum) (*Cistus ladaniferus* L.); Cinnamon (*Cinnamomum zeylanicum*); Chamomile, Roman (*Anthemis nobilis*); Chamomile, Blue (*Matricaria chamomilla*); Celery Seed (*Apium graveolins*); Cedarwood, Western Red (*Thuja plicata*); Cedarwood, Blood (*Juniperus virginiana*); Cedarwood Atlas (*Cedrus atlantica*); Carrot Seed (*Daucus carota*); Cardamon (*Elettaria cardamomum*); Caraway Seed (*Carum carvi*); Cajeput (*Melaleuca cajuputi*); Cade (*Juniperus oxy cedrus*); Birch, White (*Betula alba*); Birch, Sweet (*Betula lenta*); Bergamot (*Citrus bergamia*); Bay Laurel (*Lauras nobilis*); Basil (*Ocimum basilicum*); Basil, Holy (*Ocimum sanctum*); Basil (*Ocimum basilicum*); Balsam Poplar (*Populus balsamifera*); Balsam Peru (*Myroxylon

*balsamum*); *Angelica* (*Angelica archangelica* L.); and combinations thereof. Flavoring agents include, for example, vanillin, sage, marjoram, parsley oil, spearmint oil, cinnamon oil, oil of wintergreen (methyl salicylate), peppermint oil, clove oil, bay oil, anise oil, eucalyptus oil, citrus oils, fruit oils, and essences including those derived from lemon, orange, lime, grapefruit, apricot, banana, grape, apple, strawberry, cherry, pineapple, etc., bean and nut-derived flavors such as coffee, cocoa, cola, peanut, almond, etc., adsorbed and encapsulated flavoring agents, and mixtures thereof. Flavoring agents also include ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, alpha-irisone, propenyl guaiethol, thymol, linalool, benzaldehyde, cinnamaldehyde, N-ethyl-p-menthan-3-carboxamme, N,2,3-trimethyl-2-isopropylbutanamide, 3-L-menthoxypropane-1,2-diol, cinnamaldehyde glycerol acetal (CGA), methane glycerol acetal (MGA) and mixtures thereof. Some formulation examples include a lipophilic flavoring agent including menthol, vanillin or an essential oil (e.g., orange oil, lemon oil, clove oil, peppermint oil, spearmint oil or aniseed oil). Other flavoring agents include lemon juice concentrate, tangerine flavor, tangerine concentrate, and/or apple juice concentrate, jasmine, rooibos, and/or peppermint tea. Flavoring agents can be present in the formulation at amounts ranging from 1 to 10 mg/ml, 10 to 50 mg/ml, 50 to 100 mg/ml, 100 to 250 mg/ml, 250 to 500 mg/ml, 500 to 750 mg/ml, or 750 to 1000 mg/ml.

Sweeteners include maltose, sucrose, glucose, fructose, invert sugars and mixtures thereof. These sugars can be incorporated into the aqueous formulations in solid or liquid form. Fructose can be obtained or provided as liquid fructose, high fructose corn syrup (HFCS), dry fructose or fructose syrup. High fructose corn syrup is commercially available as HFCS-42, HFCS—55 and HFCS-90, which include 42%, 55% and 90%, respectively, by weight of the sugar solids therein of fructose. Sweeteners can be provided to some extent by other components of the aqueous formulations, such as by fruit juice, flavorants, and so forth. Sweeteners can be employed in the process of the present disclosure in amounts ranging from 0.01% to 20%, from 6% to 14%, sugar solids by weight of the aqueous formulations.

Optional artificial or noncaloric sweeteners can be used alone or in combination with carbohydrate sweeteners in beverages or beverage kits. They include, for example, saccharin, cyclamates, acetosulfame, sucralose, L-aspartyl-L-phenyalanine lower alkyl ester sweeteners (e.g., aspartame). L-aspartyl-D-alanine amides disclosed in U.S. Pat. No. 4,411,930 to Brennan et al., L-aspartyl-D-serine amides disclosed in U.S. Pat. No. 4,399,163 to Brennan et al., Laspartyl-L-1-hydroxymethyl-alkaneamide sweeteners disclosed in U.S. Pat. No. 4,338,346 to Brand, L-aspartyl-1-hydroxyethylakaneamide sweeteners disclosed in U.S. Pat. No. 4,423,029 to Rizzi, L-aspartyl-D-phenylglycine ester and amide sweeteners disclosed in European Patent Application 168,112 to J. M. Janusz, published Jan. 15, 1986, and the like. Artificial or noncaloric sweeteners, if used, are typically employed in an amount ranging from 0.01% to 1%, from 0.05% to 0.10% by weight of the beverage portion of the beverage or beverage kit.

Nutritional additives include essential oils, vitamins, minerals, and amino acids. Vitamins include Vitamin A, vitamin B1, vitamin B2, vitamin B3, vitamin B12, vitamin C, vitamin E, vitamin D, niacin (vitamin PP), biotin (vitamin H), menadione (vitamin K), folic acid, and pyridoxine (B6). Minerals include iron, zinc, calcium, phosphorus, potassium, magnesium, and fluoride. Amino acids include lysine, histidine, isoleucine, leucine, methionine, phenylalanine, threonine, tryptophan, and valine. Exemplary nutritional additives can be found in Roberts et al., Nutraceuticals: The Complete Encyclopedia of Supplements, Herbs, Vitamins, and Healing Foods (American Nutraceutical Association, 2001); in Physicians' Desk Reference for Nutritional Supplements, 1st Ed. (2001); and in The Physicians' Desk Reference for Herbal Medicines, 1st Ed. (2001), which are incorporated by reference.

Taste-masking agents include 1,3-propanediol, sodium gluconate, zinc lactate, sodium bicarbonate, ion-exchange resins, cyclodextrin inclusion compounds, adsorbates, and the like.

Aqueous formulations of the present disclosure can be formulated into an ocular formulation. Ocular formulations include aqueous formulations, suspensions (e.g., eye drops), viscous or semi-viscous gels, or other types of solid or semisolid compositions (e.g., ointments) or sustained release devices or mechanisms that are placed in or around the eye. Examples of ocular formulations include eye drops and ointments.

Aqueous formulations of the present disclosure can be formulated into an ointment formulation. An ointment is an oil-based or oil-and-water-based semi-solid or viscous formulation with a melting or softening point near body temperature. As an example, eye drops are a liquid formulation that can be applied to the eye as droplets. A gel is a jelly-like viscous formulation that includes a matrix of interacting molecules that confer viscosity, and a liquid (e.g., suspension) that is dispersed within the matrix.

Ocularly administrable formulations can also be provided with tear substitutes. "Tear substitutes" refer to molecules or compositions which lubricate or "wet," approximate the consistency of endogenous tears, aid in natural tear build-up, or otherwise provide temporary relief of eyes upon ocular administration. A variety of tear substitutes are known in the art and include: monomeric polyols, such as, glycerol, propylene glycol, and ethylene glycol; polymeric polyols such as polyethylene glycol; cellulose esters such hydroxypropylmethyl cellulose, carboxymethyl cellulose sodium and hydroxy propylcellulose; dextrans such as dextran 70; water soluble proteins such as gelatin; vinyl polymers, such as polyvinyl alcohol, polyvinylpyrrolidone, and povidone; and carbomers, such as carbomer 934P, carbomer 941, carbomer 940 and carbomer 974P. Many such tear substitutes are commercially available, which include cellulose esters such as Bion® Tears (Alcon Research, Ltd., Fort Worth, Texas, U.S.A.), Celluvisc® (Allergan, Inc., Irvine, California, U.S.A.), Genteal® (Novartis Pharmaceuticals Corporation, East Hanover, New Jersey, U.S.A.), OccuCoat® (Barnes-Hind, Inc. Clearwater, Florida, U.S.A.), Refresh® (Allergan, Inc., Irvine, California, U.S.A.), Systane® (Novartis AG, Basel, Switzerland), Systane Ultra® (Novartis AG, Basel, Switzerland), Refresh Endura® (Allergan, Inc., Irvine, California, U.S.A.), Refresh Liquigel® (Allergan, Inc., Irvine, California, U.S.A.), Teargen II™ (McKesson), Tears Naturale® (Alcon (Puerto Rico), Inc., Humacao, Puerto Rico), Tears Naturale® II (Alcon (Puerto Rico), Inc., Humacao, Puerto Rico), Tears Naturale Free® (Alcon (Puerto Rico), Inc., Fort Worth, Texas, U.S.A.), and TheraTears® (Advanced Vision Research, Inc., Ann Arbor, Michigan, U.S.A.); and polyvinyl alcohols such as Akwa Tears® (Akorn, Inc., Lake Forest, Illinois, U.S.A.), HypoTears® (Novartis Pharmaceuticals Corporation, East Hanover, New Jersey, U.S.A.), Moisture Eyes® (Bausch &

Lomb Incorporated, Rochester, New York, U.S.A.), Murine Tears® (Medtech Products, Inc., Irvington, New York, U.S.A.), Visine Tears® (Johnson & Johnson, New Brunswick, New Jersey, U.S.A.), and Soothe® (Bausch & Lomb Incorporated, Rochester, New York, U.S.A.). Tear substitutes may also include paraffins, such as the commercially available Lacri-Lube® (Allergan, Inc., Irvine, California, U.S.A.) ointments. Other commercially available ointments that are used as tear substitutes include Lubrifresh PM™ (Bausch & Lomb Incorporated), Moisture Eyes® PM (Bausch & Lomb Incorporated, Rochester, New York, U.S.A.) and Refresh P.M.® (Allergan, Inc., Irvine, California, U.S.A.).

Additional potential excipients for ocularly administrable formulations include solubilizing agents, stabilizing agents, surfactants, demulcents, viscosity modifiers, diluents, inert carriers, preservatives, binders, and/or disintegrants. Further examples of excipients include certain inert proteins such as albumins; hydrophilic polymers such as polyvinylpyrrolidone; amino acids such as aspartic acid (which may alternatively be referred to as aspartate), glutamic acid (which may alternatively be referred to as glutamate), lysine, arginine, glycine, and histidine; fatty acids and phospholipids such as alkyl sulfonates and caprylate; surfactants such as sodium dodecyl sulphate and polysorbate; nonionic surfactants such as such as TWEEN® (Tween-Croda Americas, LLC, Wilmington, DE, PLURONICS® (Pluronic-BASF Corp., Mount Olive, NJ), or a polyethylene glycol (PEG) designated 200, 300, 400, or 600; a Carbowax designated 1000, 1500, 4000, 6000, and 10000; carbohydrates such as glucose, sucrose, mannose, maltose, trehalose, and dextrins, including cyclodextrins; polyols such as mannitol and sorbitol; chelating agents such as EDTA; and salt-forming counter-ions such as sodium.

Eye drops may be made into a sterile aqueous formulation such as physiological saline, buffering solution, etc., or by combining powder compositions to be dissolved before use. Other vehicles may be chosen, as is known in the art: balance salt solution, saline solution, water soluble polyethers such as polyethylene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

For eye drops, the formulations can include concentrations of the first LAC ranging from 0.0001 to 10.0 w/v %, 0.005 to 10.0 w/v %, 0.01 to 10.0 w/v %, 0.05 to 10.0 w/v %, 0.1 to 10.0 w/v %, 0.5 to 10.0 w/v %, 1.0 to 10.0 w/v %, 20 to 10.0 w/v %, 3.0 to 10.0 w/v %, 4.0 to 10.0 w/v %, or 5.0 to 10.0 w/v %. The administration may be administered several times a day per eye, one to ten times, one to four times, or once a day. The size of the drop administered may be in the range of 10-100 ul, 10-90 ul, 10-80 ul, 10-70 ul, 10-60 ul, 10-50 ul, 10-40 ul, 10-30 ul, 20-100 ul, 20-90 ul, 20-80 ul, 20-70 ul, 20-60 ul, 20-50 ul, 20-40 ul, or 20-30 ul.

Aqueous formulations of the present disclosure can be formulated into a topical formulation. Topical formulations are formulations that are applied directly to a body surface, such as skin. Topical formulations can be in the form of foams, sprays, mousses, patches, powders, pastes, medicated plasters, creams, ointments, lotions, or gels.

Penetration enhancers increase dermal penetration and include 2-(2-ethoxyethoxy)ethanol and dimethyl isosorbide in the range of 5-30% (w/w). Other non-limiting examples of penetration enhancers include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower)alkyl esters of C6-C8 diacids such as diisopropyl adipate; monoglycerides of C8-C22 fatty acids such as glyceryl monolaurate; tetrahydrofurfuryl alcohol polyethylene glycol ether; polyethylene glycol; propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; terpenes; macrocyclic enhancers such as macrocyclic ketones, for example, 3-methylcyclopentadecanone, 9-cycloheptadecen-1-one, cyclohexadecanone, and cyclopentadecanone; macrocyclic esters such as pentadecalactone.

Example topical formulations include water. Other examples of the topical formulation are substantially or totally free of water. The water content of the topical formulation can range from 0 to 80% water.

Other components commonly used in topical formulations include antioxidants (e.g., alpha-tocopherol, beta-tocopherol, gamma-tocopherol, delta-tocopherol, butylated hydroxytoluene, butylated hydroxyanisole), stabilizers, chelating agents, softeners, lubricants, emollients, pigments, fragrances, skin soothing agents, skin healing agents and skin conditioning agents. Skin healing and skin conditioning agents include glycerol, allantoin, and bisabolol.

Common Considerations for all Products and Formulations. The following passages present considerations that are applicable to a variety of formulation types. One of ordinary skill in the art can interpret and apply these sections to formulation types described above as appropriate.

Formulations for beverages and beverage kits can include additional surfactants and/or water.

Aqueous formulations of the current disclosure can be diluted and then concentrated. As an example, Aqueous formulations may be concentrated into a liquid or solid (e.g., spray-dried particles).

Aqueous formulations can include water soluble active compounds. Example water soluble active compounds include water soluble vitamins, water soluble minerals, water soluble enzymes, and substances with a negative log P. Water soluble vitamins include ascorbic acid (vitamin C), thiamin, riboflavin, niacin, nicotinamide mononucleotide, pantethine, vitamin B6 (pyridoxine, pyridoxal, and pyridoxamine), folacin, folate, vitamin B12, biotin, choline, and pantothenic acid. Water soluble minerals include calcium, phosphorus, potassium, sodium, chloride, magnesium, iron, zinc, iodine, sulfur, cobalt, copper, fluoride, manganese, and selenium. Water soluble enzymes include bromelain, papain, lactase, beta-amylase, cellulase, lipase, and proteases. Substances with a negative log P include caffeine, theanine, theobromine, theophylline, chlorogenic acids, taurine, glucuronolactone, glucose, gamma amino butyric acid (GABA), fructose, glucose, sucrose, ribose, xylitol, inositol, aspartame, rebaudoside, soluble fiber, whey protein, ethanol, carnitine, carnosine, creatine, glycerylphosphorylcholine, beta-glucan, polyphenols, amino acids, 5-HTP, glucosamine, chondroitin, collagen, hyaluronic acid, pyrroloquinoline quinone (PQQ), glutathione, fructooligosaccharides, galactooligosaccharides, and probiotic organisms.

Aqueous formulations can include preservative compounds. Suitable preservatives include benzalkonium chloride, thimerosal, chlorobutanol, methyl paraben, propyl paraben, phenylethyl alcohol, edetate disodium, sorbic acid, Onamer M, or other agents known to those skilled in the art. Some examples of suitable preservatives include any food-grade preservative such as antioxidant preservatives and antimicrobial preservatives. Antioxidant preservatives include ascorbyl palmitate, ascorbic acid, butylated hydroxyanisole (BHA) butylated hydroxytoluene (BHT), citric acid, rosmarinic acid, sulfites, tertiary butylhydroquinone (TBHQ), tocopherols, and salts and mixtures thereof. Antimicrobial preservatives include acetic acid, benzoic acid, potassium sorbate, natamycin, nisin, nitrates, nitrites, propionic acid, rosmarinic acid, sorbic acid, sulfites, sodium hexametaphosphate, sulfur dioxide, and salts and mixtures thereof. Some preservative classes include antibiotics, antimicrobials, antifungals, and antivirals. The preservative may be a water-phase preservative. Water-phase preservatives include etheylenediaminetetraacetic acid (EDTA), citric acid, potassium sorbate, and sodium benzoate. Preservatives may be employed at a level from 0.004% to 0.02%, from 0.001% to 0.01%, from 0.001% to 0.008%, or 0.005% to 0.006%, from 0.02% to 0.3%, from 0.04% to 0.2%, or 0.1% to 0.2% by weight of a formulation.

Aqueous formulations can include pH modifiers compounds. Suitable pH modifiers include citric acid, tartaric acid, phosphoric acid, hydrochloric acid, maleic acid, sodium hydroxide, disodium hydrogen phosphate, sodium acetate, sodium bicarbonate, sodium phosphate tribasic, dipotassium hydrogen phosphate, acetic acid, lactic acid, fumaric acid, adipic acid, sulfuric acid, salts thereof, and combinations thereof. The pH of the aqueous formulation will be buffered. In some examples the pH modifier includes a buffer to maintain a physiologically compatible pH range. Buffers include acetate, bicarbonate, citrate, and phosphate. In some examples, the aqueous formulation has a pH from 2 to 9, the aqueous formulation has a pH from 6.5 to 7.5, or the aqueous formulation has a pH of 7. Acidity can be adjusted to and maintained within the requisite range by known and conventional methods, e.g., the use of acid buffers. Typically, acidity is a balance of maximum acidity for microbial inhibition and optimum acidity for aqueous formulation characteristics (e.g., flavor or activity).

Aqueous formulations can include colorants. Coloring agents include red, black and yellow iron oxides and FD&C dyes such as FD&C Blue No. 2, FD&C Red No. 40. The coloring agents that may be used in food include carotene, curcumin, riboflavin, carmine, turmeric, annatto, cochineal, betanin, saffron, paprika, elderberry, brilliant blue, indigotine, fast green, allura red, erythrosine, tartrazine, sunset yellow, and caramel.

Aqueous formulations can include rheology modifiers. Viscosity modifiers include cellulose or cellulose derivatives such as ethylcellulose, hydroxyethyl cellulose (HEC), hydroxypropyl cellulose (HPC), carboxymethylcellulose, sodium hydroxypropyl methylcellulose (HPMC), methylcellulose, methylethylcellulose, sodium carboxymethylcellulose, polyvinylpyrrolidone, polyvinylpolypyrrolidone (crospovidone), Carbopol (carbomer), and sodium hyaluronate (hyaluronic acid), Aerosil, cetostearyl alcohol, Gelucires 33/01, 39/01 and 43/01, glyceryl behenate, glyceryl palmitostearate, Softisans 100, 142, 378 and 649, stearyl alcohol carbomer, xanthan gum, maltodextrin, gum arabic, acacia gum, ghatti gum, pectin, low methoxyl pectin, high methoxyl pectin, amidated pectin, tragacanth, povidone and polyvinyl alcohol.

Lubricants include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof.

Thickeners include xanthan gum, carboxymethylcellulose, propylene glycol alginate, gellan gum, guar gum, pectin, tragacanth gum, gum acacia, locust bean gum, as well as mixtures of these thickeners.

Formulations of the current application may include a sterile unit dose type containing no preservatives, in multidose form, and/or packaged with preservatives to prevent microbial contamination during use.

Formulations can contain an amount of first LAC selected from 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, or more than 100 mg.

Formulations described in the current disclosure can contain a concentration of first LAC ranging from 0.0001 to 10.0 w/v %, 0.005 to 10.0 w/v %, 0.01 to 10.0 w/v %, 0.05 to 10.0 w/v %, 0.1 to 10.0 w/v %, 0.5 to 10.0 w/v %, 1.0 to 10.0 w/v %, 20 to 10.0 w/v %, 3.0 to 10.0 w/v %, 4.0 to 10.0 w/v %, or 5.0 to 10.0 w/v %. These formulations may be applied several times a day, one to six times, one to four times, one to two times, or once a day.

Formulations of the present disclosure can be administered to subjects (humans, veterinary animals (dogs, cats, reptiles, birds, etc.) livestock (horses, cattle, goats, pigs, chickens, etc.) and research animals (monkeys, rats, mice, fish, etc.); usually at an effective amount is administered to the subject. An "effective amount" is the amount of a formulation necessary to result in a desired physiological change in the subject.

For administration, effective amounts (also referred to herein as doses) can be initially estimated based on results from in vitro assays and/or animal model studies. Such information can be used to determine useful doses more accurately in subjects of interest. The actual dose amount administered to a particular subject can be determined by the subject, a physician, veterinarian, or researcher taking into account parameters such as physical and physiological factors including target, body weight, severity of a condition, gender, age, symptoms to be treated, previous or concurrent therapeutic interventions, desirable effects, route of administration, and period of administration.

The formulations of the present disclosure may be administered several times per day, one to four times per day, one to three times per day, one to two times per day, or once per day. Each administration can include one dose or several doses. The formulation can be administered as several units per administration, one to four units, one to three units, one to two units, or one unit per administration. Units can be any of the administrable formulations described above including dry powder, foams, gels, granules, inhalers, liquids, lotions, lozenges, mists, oils, ointments, pastes, pills, powder, pressurized atomizers, solutions, sprays, strips, suspensions, syrups, tablets, troches, or wafers. If the formulation is a drop, the formulation can be administered as several drops per administration, one to four drops, one to three drops, one to two drops, or one drop per administration. If the formulation is a spray, the formulation can be administered as several sprays per administration, one to four sprays, one to three sprays, one to two sprays, or one spray per administration. If the formulation is a capsule, the formulation can be administered as several capsules per administration, one to four capsules, one to three capsules, one to two capsules, or one capsule per administration. If the formulation is a tablet, the formulation can be administered as several tablets per administration, one to four tablets, one to three tablets, one to two tablets, or one tablet per administration.

Effective amounts of LAC can include 0.1 ug/kg to 5 mg/kg body weight, 0.5 ug/kg to 2 mg/kg, or 1 mg/kg to 4 mg/kg. Effective amounts to administer can include greater than 0.1 ug/kg, greater than 0.6 ug/kg, greater than 1 mg/kg, greater than 2 mg/kg, greater than 3 mg/kg, greater than 4 mg/kg, or greater than 5 mg/kg of body weight.

The Exemplary Embodiments and Example below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLES

In an embodiment a method of producing a cannabinoid or API infused formulation is presented where the surfactant and glycoside are added to the aqueous phase and placed under sonication, high pressure homogenization and temperature.

In an embodiment a method of producing a cannabinoid or API infused formulation is presented where the temperature is in the range is from about 20° C. to about 100° C., ultrasound frequency from 20-40 kHz, residence time 10 s to 60 min, power from 10 w to 1 kW, and ultrasonic energy from 1000 J to 5 MJ.

In an embodiment a method of producing a cannabinoid or API infused formulation is presented where the high-pressure homogenization has a shear rate at around $1\times10^8$/s, temperature is from about 10° C. to about 80° C., and velocity is from about 200 m/s to about 400 m/s.

In an embodiment a method of producing a cannabinoid or API infused formulation is presented where the aqueous formulation has five to ten more times LAC than an individual glycoside within the aqueous formulation.

In an embodiment a method of producing a cannabinoid or API infused formulation is presented where the aqueous formulation has two times more LAC than the combination of two glycosides within the aqueous formulation.

Example Formulations

Formulation 1. The aqueous formulation of embodiment 1, including 30-40 g LAC, 3-7 g sucrose acetate isobutyrate, 2-6 g surfactant, 3-7 g rebaudoside A, 4-8 g glycoside, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate and 580-630 g water.

Formulation 2. The aqueous formulation of embodiment 1, including 35 g LAC, 4 g sucrose acetate isobutyrate, 4 g surfactant, 5 g rebaudoside A, 6 g glycoside, 0.4 g tocopherol, 0.08 g ascorbyl palmitate, 0.80 g ascorbic acid, 0.18 g sodium benzoate, 0.2 g potassium sorbate, and 610 or 611 g water.

Formulation 3. The aqueous formulation of embodiment 1, including 35.85 g LAC, 4.93 g sucrose acetate isobutyrate, 3.96 g surfactant, 4.70 g rebaudoside A, 6.26 g glycoside, 0.41 g tocopherol, 0.08 g ascorbyl palmitate, 0.80 g ascorbic acid, 0.18 g sodium benzoate, 0.24 g potassium sorbate, and 611.50 g water.

Formulation 4. The aqueous formulation embodiment 1, including 30-40 g LAC, 3-7 g sucrose acetate isobutyrate, 2-6 g surfactant, 3-7 g glycoside, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 5. The aqueous formulation of embodiment 1, including 35 g LAC, 4 g sucrose acetate isobutyrate, 4 g surfactant, 5 g glycoside, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 6. The aqueous formulation of embodiment 1, including 35.85 g LAC, 4.93 g sucrose acetate isobutyrate, 3.96 g surfactant, 4.70 g glycoside, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 7. The aqueous formulation of embodiment 1, including 35 g LAC, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 8. The aqueous formulation of embodiment 1, including 35.85 g LAC, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 9. The aqueous formulation of embodiment 1, including 30-40 g cannabidiol, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 10. The aqueous formulation of embodiment 1, including 35 g cannabidiol, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 11. The aqueous formulation of embodiment 1, including 35.85 g cannabidiol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 12. The aqueous formulation of embodiment 1, including 30-40 g cannabidiol, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 13. The aqueous formulation of embodiment 1, including 35 g cannabidiol, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 14. The aqueous formulation of embodiment 1, including 35.85 g cannabidiol, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 15. The aqueous formulation of embodiment 1, including 30-40 g cannabidiol, 3-7 g triethyl citrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 16. The aqueous formulation of embodiment 1, including 35 g cannabidiol, 4 g triethyl citrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 17. The aqueous formulation of embodiment 1, including 35.85 g cannabidiol, 4.93 g triethyl citrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 18. The aqueous formulation of embodiment 1, including 30-40 g tetrahydrocannabinol, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 19. The aqueous formulation of embodiment 1, including 35 g tetrahydrocannabinol, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 20. The aqueous formulation of embodiment 1, including 35.85 g tetrahydrocannabinol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 21. The aqueous formulation of embodiment 1, including 30-40 g cannabigerol, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 22. The aqueous formulation of embodiment 1, including 35 g cannabigerol, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 23. The aqueous formulation of embodiment 1, including 35.85 g cannabigerol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 24. The aqueous formulation of embodiment 1, including 30-40 g cannabidiol, 3-7 g sucrose acetate isobutyrate, 2-6 g saponin, 3-7 g rebaudoside M, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 25. The aqueous formulation of embodiment 1, including 35 g cannabidiol, 4 g sucrose acetate isobutyrate, 4 g saponin, 5 g rebaudoside M, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 26. The aqueous formulation of embodiment 1, including 35.85 g cannabidiol, 4.93 g sucrose acetate isobutyrate, 3.96 g saponin, 4.70 g rebaudoside M, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 27. The aqueous formulation of embodiment 1, including 30-40 g cannabidiol, 3-7 g sucrose acetate isobutyrate, 2-6 g saponin, 3-7 g rebaudoside A, 4-8 g isomogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 28. The aqueous formulation of embodiment 1, including 35 g cannabidiol, 4 g sucrose acetate isobutyrate, 4 g saponin, 5 g rebaudoside A, 6 g isomogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 29. The aqueous formulation of embodiment 1, including 35.85 g cannabidiol, 4.93 g sucrose acetate isobutyrate, 3.96 g saponin, 4.70 g rebaudoside A, 6.26 g isomogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 30. The aqueous formulation of embodiment 1, including 30-40 g curcumin, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 31. The aqueous formulation of embodiment 1, including 35 g curcumin, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 32. The aqueous formulation of embodiment 1, including 35.85 g curcumin, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 33. The aqueous formulation of embodiment 1, including 30-40 g melatonin, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Formulation 34. The aqueous formulation of embodiment 1, including 35 g melatonin, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Formulation 35. The aqueous formulation of embodiment 1, including 35.85 g melatonin, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 36. The aqueous formulation of embodiment 1, including 30-40 g cannabidiol, 3-7 g sucrose acetate isobutyrate, 2-6 g saponin, 3-7 g rebaudoside A, 4-8 g mogroside V, and 580-630 g water.

Formulation 37. The aqueous formulation of embodiment 1, including 35 g cannabidiol, 4 g sucrose acetate isobutyrate, 4 g saponin, 5 g rebaudoside A, 6 g mogroside V, and 610 or 611 g water.

Formulation 38. The aqueous formulation of embodiment 1, including 35.85 g cannabidiol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Formulation 39. The aqueous formulation of embodiment 1, including 30-40 g cannabidiol, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.1-0.3 g sodium benzoate, 0.1-0.3 g potassium sorbate, 4-8 g sucrose, and 580-630 g water.

Formulation 40. The aqueous formulation of embodiment 1, including 35 g cannabidiol, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.2 g sodium benzoate, 0.2 g potassium sorbate, 6 g sucrose, and 610 or 611 g water.

Formulation 41. The aqueous formulation of embodiment 1, including 35.85 g cannabidiol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, 6.12 g sucrose, and 611.50 g water.

Formulation 42. The aqueous formulation of embodiment 1, including 8-12 g cannabidiol, 14-18 g all-rac-alpha-tocopherol, 0.25-2 g rebaudoside A, 0.25-2 g mogroside V, 0.05-0.2 g ascorbyl palmitate, 1-3 g tween 80, 2-5 g span 80, 0.01-0.05 g sodium benzoate, 0.02-0.06 g potassium sorbate, and 65-70 g water.

Formulation 43. The aqueous formulation of embodiment 1, including 10 g cannabidiol, 16 g all-rac-alpha-tocopherol, 1 g rebaudoside A, 1 g mogroside V, 0.10 g ascorbyl palmitate, 2 g tween 80, 3 or 4 g span 80, 0.03 g sodium benzoate, 0.04 g potassium sorbate, and 67 g water.

Formulation 44. The aqueous formulation of embodiment 1, including 10 g cannabidiol, 16 g all-rac-alpha-tocopherol, 0.61 g rebaudoside A, 0.82 g mogroside V, 0.10 g ascorbyl palmitate, 1.98 g tween 80, 3.52 g span 80, 0.03 g sodium benzoate, 0.04 g potassium sorbate, and 66.9 g water.

Formulation 45. The aqueous formulation of embodiment 1, includes 5-7 g ubiquinone, 0.25-2 g saponin, 0.25-2 g rebaudoside A, 0.25-2 g mogroside V, 0.01-0.05 g sodium benzoate, 0.02-0.06 g potassium sorbate, and 90-95 g water.

Formulation 46. The aqueous formulation of embodiment 1, including 6 g ubiquinone, 1 g saponin, 1 g rebaudoside A, 1 g mogroside V, 0.03 g sodium benzoate, 0.04 g potassium sorbate, and 92 g water.

Formulation 47. The aqueous formulation of embodiment 1, includes 5.99 g ubiquinone, 0.78 g saponin, 0.61 g rebaudoside A, 0.82 g mogroside V, 0.03 g sodium benzoate, 0.04 g potassium sorbate, and 91.73 g water.

Example Kit Compositions

In another aspect a kit for manufacturing aqueous formulations is presented where the kit comprises: at least one glycoside; at least one surfactant; and a lipophilic active component (LAC); where the aqueous formulation is stable.

In an embodiment a kit for manufacturing aqueous formulations is presented, wherein the contents of the kit are added to water or a water solution.

In an embodiment a kit for manufacturing aqueous formulations is presented, wherein the contents of the kit are added to glycerin, propylene glycol, or combinations thereof.

In an embodiment a kit for manufacturing aqueous formulations is presented, wherein citric acid, sodium citrate, magnesium citrate, calcium citrate, potassium citrate, phosphoric acid and phosphate salts, lactic acid and lactate salts, acetic acid and acetate salts, sucrose, fructose, sorbitol, xylitol, maltitol, sucralose, saccharin, stevia, carbon dioxide, salicylic acid, benzoyl peroxide, fragrances, natural and artificial flavoring, colorants, sodium benzoate, potassium sorbate, preservatives, pigments, active pharmaceutical agent, or any combinations thereof is added to the kit.

In an embodiment a kit for manufacturing aqueous formulations is presented, the kit further comprising a stabilizing agent.

In an embodiment a kit for manufacturing aqueous formulations is presented, wherein the stabilizing agent is xanthan gum, locust bean gum, guar gum, konjac gum, gum arabic, hydroxyethyl cellulose, carboxy methyl cellulose, alginates, kappa-carrageenan, lambda-carrageenan, iota-carrageenan, pectin, or any combinations thereof.

In an embodiment a kit for manufacturing aqueous formulations is presented, the kit further comprising a weighting agent.

In an embodiment a kit for manufacturing aqueous formulations is presented, wherein the lipophilic weighting agent is sucrose acetate isobutyrate, brominated vegetable oil, ester gum, damar gum, octenyl succinate anhydrate, or combinations thereof.

In an embodiment a kit for manufacturing aqueous formulations is presented, wherein the kit is used to make a beverage product, a cosmetic product, a nasal product, a cream, a lotion, an ointment, or a spray.

Kit Composition 1: 30-40 g LAC, 3-7 g sucrose acetate isobutyrate, 2-6 g surfactant, 3-7 g rebaudoside A, 4-8 g glycoside, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate and 580-630 g water.

Kit Composition 2: 35 g LAC, 4 g sucrose acetate isobutyrate, 4 g surfactant, 5 g rebaudoside A, 6 g glycoside, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 3: 35.85 g LAC, 4.93 g sucrose acetate isobutyrate, 3.96 g surfactant, 4.70 g rebaudoside A, 6.26 g glycoside, 0.41 g tocopherol, 0.08 g ascorbyl palmitate, 0.80 g ascorbic acid, 0.18 g sodium benzoate, 0.24 g potassium sorbate, and 611.50 g water.

Kit Composition 4: 30-40 g LAC, 3-7 g sucrose acetate isobutyrate, 2-6 g surfactant, 3-7 g glycoside, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 5: 35 g LAC, 4 g sucrose acetate isobutyrate, 4 g surfactant, 5 g glycoside, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 6: 35.85 g LAC, 4.93 g sucrose acetate isobutyrate, 3.96 g surfactant, 4.70 g glycoside, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 7: 30-40 g LAC, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 8: 35 g LAC, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 9: 35.85 g LAC, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 10: 30-40 g cannabidiol, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 11: 35 g cannabidiol, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 12: 35.85 g cannabidiol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 13: 30-40 g cannabidiol, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 14: 35 g cannabidiol, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 15: 35.85 g cannabidiol, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 16: 30-40 g cannabidiol, 3-7 g triethyl citrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 17: 35 g cannabidiol, 4 g triethyl citrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 18: 35.85 g cannabidiol, 4.93 g triethyl citrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 19: 30-40 g tetrahydrocannabinol, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 20: 35 g tetrahydrocannabinol, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 21: 35.85 g tetrahydrocannabinol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 22: 30-40 g cannabigerol, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 23: 35 g cannabigerol, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 24: 35.85 g cannabigerol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 25: 30-40 g cannabidiol, 3-7 g sucrose acetate isobutyrate, 2-6 g saponin, 3-7 g rebaudoside M, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 26: 35 g cannabidiol, 4 g sucrose acetate isobutyrate, 4 g saponin, 5 g rebaudoside M, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 27: 35.85 g cannabidiol, 4.93 g sucrose acetate isobutyrate, 3.96 g saponin, 4.70 g rebaudoside M, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 28: 30-40 g cannabidiol, 3-7 g sucrose acetate isobutyrate, 2-6 g saponin, 3-7 g rebaudoside A, 4-8 g isomogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 29: 35 g cannabidiol, 4 g sucrose acetate isobutyrate, 4 g saponin, 5 g rebaudoside A, 6 g isomogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 30: 35.85 g cannabidiol, 4.93 g sucrose acetate isobutyrate, 3.96 g saponin, 4.70 g rebaudoside A, 6.26 g isomogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 31: 30-40 g curcumin, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 32: 35 g curcumin, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 33: 35.85 g curcumin, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 34: 30-40 g melatonin, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.10-0.26 g sodium benzoate, 0.1-0.3 g potassium sorbate, and 580-630 g water.

Kit Composition 35: 35 g melatonin, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.18 g sodium benzoate, 0.2 g potassium sorbate, and 610 or 611 g water.

Kit Composition 36: 35.85 g melatonin, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, and 611.50 g water.

Kit Composition 37: 30-40 g cannabidiol, 3-7 g sucrose acetate isobutyrate, 2-6 g saponin, 3-7 g rebaudoside A, 4-8 g mogroside V, and 580-630 g water.

Kit Composition 38: 35 g cannabidiol, 4 g sucrose acetate isobutyrate, 4 g saponin, 5 g rebaudoside A, 6 g mogroside V, and 610 or 611 g water.

Kit Composition 39: 35.85 g cannabidiol, 4.93 g sucrose acetate isobutyrate, 3.96 g saponin, 4.70 g rebaudoside A, 6.26 g mogroside V, and 611.50 g water.

Kit Composition 40: 30-40 g cannabidiol, 3-7 g sucrose acetate isobutyrate, 2-6 g saponin, 3-7 g rebaudoside A, 4-8 g mogroside V, 0.2-0.6 g tocopherol, 0.06-0.10 g ascorbyl palmitate, 0.60-1.0 g ascorbic acid, 0.1-0.3 g sodium benzoate, 0.1-0.3 g potassium sorbate, 4-8 g sucrose, and 580-630 g water.

Kit Composition 41: 35 g cannabidiol, 4 g sucrose acetate isobutyrate, 4 g saponin, 5 g rebaudoside A, 6 g mogroside V, 0.4 g tocopherol, 0.08 g ascorbyl palmitate, 0.80 g ascorbic acid, 0.2 g sodium benzoate, 0.2 g potassium sorbate, 6 g sucrose, and 610 or 611 g water.

Kit Composition 42: 35.85 g cannabidiol, 4.93 g sucrose acetate isobutyrate, 3.96 g saponin, 4.70 g rebaudoside A, 6.26 g mogroside V, 0.41 g tocopherol, 0.08 g ascorbyl palmitate, 0.80 g ascorbic acid, 0.18 g sodium benzoate, 0.24 g potassium sorbate, 6.12 g sucrose, and 611.50 g water.

Kit Composition 43: 18-12 g cannabidiol, 14-18 g all-rac-alpha-tocopherol, 0.25-2 g rebaudoside A, 0.25-2 g mogroside V, 0.05-0.2 g ascorbyl palmitate, 1-3 g tween 80, 2-5 g span 80, 0.01-0.05 g sodium benzoate, 0.02-0.06 g potassium sorbate, and 65-70 g water.

Kit Composition 44: 10 g cannabidiol, 16 g all-rac-alpha-tocopherol, 1 g rebaudoside A, 1 g mogroside V, 0.10 g ascorbyl palmitate, 2 g tween 80, 3 or 4 g span 80, 0.03 g sodium benzoate, 0.04 g potassium sorbate, and 67 g water.

Kit Composition 45: 10 g cannabidiol, 16 g all-rac-alpha-tocopherol, 0.61 g rebaudoside A, 0.82 g mogroside V, 0.10 g ascorbyl palmitate, 1.98 g tween 80, 3.52 g span 80, 0.03 g sodium benzoate, 0.04 g potassium sorbate, and 66.9 g water.

Kit Composition 46: 5-7 g ubiquinone, 0.25-2 g saponin, 0.25-2 g rebaudoside A, 0.25-2 g mogroside V, 0.01-0.05 g sodium benzoate, 0.02-0.06 g potassium sorbate, and 90-95 g water.

Kit Composition 47: 6 g ubiquinone, 1 g saponin, 1 g rebaudoside A, 1 g mogroside V, 0.03 g sodium benzoate, 0.04 g potassium sorbate, and 92 g water.

Kit Composition 48: 5.99 g ubiquinone, 0.78 g saponin, 0.61 g rebaudoside A, 0.82 g mogroside V, 0.03 g sodium benzoate, 0.04 g potassium sorbate, and 91.73 g water.

Unless otherwise indicated, the practice of the present disclosure can standard definitions of chemistry, organic chemistry, and biochemistry. These definitions are described in, for example, Harcourt et al., Holt McDougal Modern Chemistry: Student Edition (2018); J. Karty, Organic Chemistry Principles and Mechanisms (2014); Nelson et al., Lehninger Principles of Biochemistry 5th edition (2008); Skoog et al., Fundamentals of Analytical Chemistry (8th Edition); Atkins et al., Atkins' Physical Chemistry (11th Edition).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of" The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability to obtain a claimed effect according to a relevant parameter described in the current disclosure.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

The embodiments of the invention in which an exclusive property or privilege is claimed are defined as follows:

1. An aqueous formulation comprising:

at least one glycoside comprising at least one terpene glycoside;

at least one surfactant;

a lipophilic active component (LAC);

wherein the LAC comprises a first LAC comprising at least one cannabinoid;

at least one additional lipophilic component, wherein the combination of the LAC and the at least one additional lipophilic component is a total lipophilic content;

wherein the aqueous formulation has a concentration of the first LAC ranging from about 0.0001 w/v % to about 50.0 w/v %;

wherein a ratio of the at least one surfactant to the at least one terpene glycoside is 5.9 parts-80 parts of the at least one surfactant to 20 parts-94.1 parts of the at least one terpene glycoside;

wherein a ratio of the total lipophilic content to the combination of the at least one surfactant and the at least one terpene glycoside is 45.5 parts-90.3 parts of the total lipophilic content to 9.7 parts-54.5 parts of the combined at least one surfactant plus at least one terpene glycoside;

wherein the ratio of the LAC to an individual glycoside is from about 2:1 w/w to about 20:1 w/w;

wherein the ratio of the LAC to a total number of glycosides is from about 2:1 w/w to about 20:1 w/w; and wherein the aqueous formulation is a stable emulsion.

2. The aqueous formulation of claim 1, wherein the terpene glycoside is selected from the classes of steviol, curcurbitane, diterpenoid, triterpenoid, steroid glycoside, rebaudioside, mogroside, thioglycoside, iridoid glycoside, cardiac glycoside, phenolic glycoside, flavonoid glycoside, hesperidin, naringin, rutin, quercitrin, cyanogenic glycosides, benzo-gamma-pyrone, alcoholic glycosides, anthraquinone glycosides, coumarin glycosides, chromone glycosides, or any combination thereof.

3. The aqueous formulation of claim 1, wherein the surfactant is selected from an ionic surfactant, an anionic surfactant, a cationic surfactant, a zwitterionic surfactant, a non-ionic surfactant or any combination thereof.

4. The aqueous formulation of claim 3, wherein the surfactant is a sorbitan fatty acid ester, polyethylene glycol sorbitan fatty acid ester, saturated polyglycolized glyceride, amyrin, furostan, QS-21, glycyrrhizic acid, escin, tea saponin, bidesmosidic saponin from *quillaja, quillaia*, polyethylene glycol stearate, polyethylene glycol hydrogenated castor oil, propylene glycol laurate, D-alpha-tocopherol polyethylene glycol 1000 succinate (TPGS), lecithin, sucrose laurate, sucrose palmitate, sucrose stearate, gamma-cyclodextrin, beta-cyclodextrin, whey protein, caseinate, polyethylene glycol hydroxystearate polyoxyl-10-oleyl ether, polyethylene glycol glyceride, polysorbate 20, polysorbate 40, polysorbate 60, polysorbate 65, polysorbate 80, polysorbate 85, sorbitan monolaurate, sorbitan monopalmitate, sorbitan monostearate, sorbitan tristearate, sorbitan monoleate, sorbitan trioleate, coco glucoside, decyl glucoside, caprylyl glucoside, cocamidopropyl betaine, coco betaine, disodium laureth sulfosuccinate, lauryl glucoside, coco glucoside, decyl glucoside, lauryl glucoside, disodium laureth sulfosuccinate, sodium coco sulfate, soap nuts, yucca extract, shikakai powder, soapwort, cholesterol, phytosterol, monoglyceride, lanolin, or combinations thereof.

5. The aqueous formulation of claim 1, wherein the cannabinoid is a naturally derived cannabinoid, a synthetically modified cannabinoid from a natural cannabinoid, a synthetic cannabinoid, a cannabinoid that is modified by action of the atmosphere, an endocannabinoid, or any combination thereof.

6. The aqueous formulation of claim 1, wherein the cannabinoid is tetrahydrocannabinol acid (THCA), delta-9-tetrahydrocannabinol (delta-9-THC), cannabidiol acid (CBDA), cannabidiol (CBD), delta-8-tetrahydrocannabinol (delta-8-THC), cannabinol (CBN), cannabichromene (CBC), cannabidivarin (CBDV), cannabigerolic acid (CBGA), cannabigerol (CBG), cannabicyclol (CBL), tetrahydrocannabivarin (THCV), tetrahydrocannabiphorol (THCP), dexanabinol (HU-211), 1,1-dimethylheptyl-11-hydroxy-tetrahydrcannabinol (HU-210), 1-pentyl-3-(4-methoxybenzoyl)indole (RCS-4), cannabicyclohexanol (CP 47,497), cannabipiperidiethanone (CPE), N-(1-adamantyl)-1-pentyl-1H-indole-3-carboxamide (APICA), AZD-1940, 1-pentyl-3-(2-methoxyphenylacetyl)indole (JWH-250), JWH-051, JWH-176, AB-FUBINACA, AB-FUBINACA, CUMYL-CBMICA, FUB-PB-22, THJ-2201, JWH-203, 5F, AB-FUPPYCA, WIN 55,202-2, PB-22, FAB-144, UR-144, anandamide (AEA), 2-arachidonoyl glycerol (2-AG), 1-(2-cyclohexylethyl)-3-(2-methoxyphenylacetyl)indole (RS-8), 1-pentyl-3-(4-methoxybenzoyl)indole (RSC-4), (1-pentyl-3-(1-naphthoyl)indole (JWH-018), or any combination thereof.

7. The aqueous formulation of claim 1, wherein the LAC further comprises additional lipophilic component or combinations of additional lipophilic components.

8. The aqueous formulation of claim 7, wherein the additional lipophilic component or combinations of additional lipophilic components are oils, fatty esters, hydrocarbon oils, silicones, waxes, fatty alcohols, lipophilic vitamins, phospholipids, white/yellow paraffin, hard paraffin, microcrystalline wax, petrolatum, cholesterol, bees wax, spermaceti wax, plastibase, ceresin, or any combinations thereof.

9. The aqueous formulation of claim 8, wherein the oils are corn oil, castor oil, soybean oil, linseed oil, sunflower oil, safflower oil, canola coil, peanut oil, cacao butter, coconut oil, cotton seed oil, sesame oil, almond oil, hydrogenated sulphated castor oil, hempseed oil, medium chain triglycerides, monoglycerides, diglycerides, triglycerides, or any combinations thereof.

10. The aqueous formulation of claim 8, wherein the lipophilic vitamins are alpha-carotene, beta-carotene, gamma-carotene, delta-carotene, epsilon-carotene, lycopene, retinol, retinal, esters of retinol, a carotenoid, ergocalciferol, cholecalciferol, alpha-tocopherol, beta-tocopherol, gamma-tocopherol, delta-tocopherol, alpha-tocotrienol, beta-tocotrienol, gamma-tocotrienol, delta-tocotrienol, phylloquinone, phytonadione, menaquinone, menaphthone, menadione, anthocyanins, catechins, flavonoids, isoflavonoids, polyphenols, zoochemicals, xanthophylls, astaxanthin, cryptoxanthin, zeaxanthin, antheraxanthin, violaxanthin, diatoxanthin, lutein, neurosporene, phytol, isophytol, essential fatty acids, omega-3, omega-6, omega-9, or any combination thereof.

11. The aqueous formulation of claim 1 further comprising a stabilizing agent.

12. The aqueous formulation of claim 11, wherein the stabilizing agent is xanthan gum, locust bean gum, guar gum, konjac gum, gum arabic, hydroxyethyl cellulose, carboxy methyl cellulose, alginates, kappa-carrageenan, lambda-carrageenan, iota-carrageenan, pectin, beta-lactoglobulin, whey protein, polyelectrolites, starch, modified starch, galactomannans, alginates, curdlan, gellan gum, carob gum, cellulose, gelatin, pectin, or any combinations thereof.

13. The aqueous formulation of claim 1 further comprising a lipophilic weighting agent.

14. The aqueous formulation of claim 13, wherein the lipophilic weighting agent is sucrose acetate isobutyrate, brominated vegetable oil, ester gum, damar gum, octenyl succinate anhydrate, or combinations thereof.

15. The aqueous formulation of claim 1, wherein the formulation is a beverage product, an ingestible product, an inhalable product, an ocular product, a topical product, or a pharmaceutical product.

16. The aqueous formulation of claim 15, wherein the beverage product is beer, coffee, tea, soda, juice or juice flavored drink, carbonated, or any combination thereof.

17. The aqueous formulation of claim 15, wherein the topical product is a cream, a lotion, an ointment, a gel, a paste, a spray, transdermal patch or any combination thereof.

18. The aqueous formulation of claim 1, wherein the aqueous formulation further compromises a plurality of glycerides.

19. The aqueous formulation of claim 1, wherein the at least one glycoside is a mogroside or a rebaudioside.

20. The aqueous formulation of claim 1, wherein the at least one glycoside is a terpene glycoside.

21. The aqueous formulation of claim 1, wherein the combination of ratios of the at least one terpene glycoside, the at least one surfactant, and the LAC result in the aqueous formulation remaining in a consumable and/or useable condition for at least 6-months and contains particles that resist Ostwald ripening.

* * * * *